United States Patent
Renaud et al.

(10) Patent No.: US 9,995,668 B2
(45) Date of Patent: Jun. 12, 2018

(54) APPARATUS FOR MANIPULATING, MODIFYING AND CHARACTERIZING PARTICLES IN A MICRO CHANNEL

(75) Inventors: Philippe Renaud, Préverenges (CH);
Pontus Linderholm, Lausanne (CH);
Thomas Braschler, Lausanne (CH);
Nicolas Demierre, Lausanne (CH);
Urban Seger, Lausanne (CH)

(73) Assignee: Ecole Polytechnique Fédérale de Lausanne (EPFL), Lausanne (CH)

( * ) Notice: Subject to any disclaimer, the term of this patent is extended or adjusted under 35 U.S.C. 154(b) by 1252 days.

(21) Appl. No.: 12/278,087

(22) PCT Filed: Feb. 1, 2007

(86) PCT No.: PCT/IB2007/050338
§ 371 (c)(1),
(2), (4) Date: Apr. 29, 2009

(87) PCT Pub. No.: WO2007/088517
PCT Pub. Date: Aug. 9, 2007

(65) Prior Publication Data
US 2010/0006441 A1    Jan. 14, 2010

(30) Foreign Application Priority Data
Feb. 1, 2006 (WO) .................. PCT/IB2006/050345

(51) Int. Cl.
*G01N 15/12* (2006.01)
*B01L 3/00* (2006.01)
*B03C 5/02* (2006.01)

(52) U.S. Cl.
CPC ........ *G01N 15/12* (2013.01); *B01L 3/502746* (2013.01); *B01L 3/502761* (2013.01);
(Continued)

(58) Field of Classification Search
CPC ......... B01L 3/502746; B01L 3/502761; B01L 2200/0647; B01L 2200/0668;
(Continued)

(56) References Cited

U.S. PATENT DOCUMENTS 1,498,911 A   6/1924 Stafford
4,484,134 A   11/1984 Halloran
(Continued)

FOREIGN PATENT DOCUMENTS

EP     0 130 530       1/1985
WO     WO 99/52640     10/1999
(Continued)

OTHER PUBLICATIONS

Arnold WM, Schwan HP and Zimmermann U: 'Surface conductance and other properties of latex-particles measured by electrorotation' *Journal of Physical Chemistry 91*, 5093-98, 1987.
(Continued)

*Primary Examiner* — Maris R Kessel
(74) *Attorney, Agent, or Firm* — Nixon & Vanderhye P.C.

(57) ABSTRACT

Microfluidic system comprising a space for containing a liquid and at least one lateral chamber in communication with said space, said lateral chamber containing a metal electrode. The lateral chamber and the space are designed to be filled by the same or different liquid when the system is active.

20 Claims, 10 Drawing Sheets

(52) U.S. Cl.
CPC ....... B03C 5/026 (2013.01); *B01L 2200/0647* (2013.01); *B01L 2200/0668* (2013.01); *B01L 2200/12* (2013.01); *B01L 2200/147* (2013.01); *B01L 2300/0645* (2013.01); *B01L 2300/0864* (2013.01); *B01L 2400/0415* (2013.01); *B01L 2400/0424* (2013.01); *B01L 2400/086* (2013.01)

(58) Field of Classification Search
CPC ........... B01L 2200/12; B01L 2200/147; B01L 2400/086; B01L 2400/0424; B01L 2300/0864; B01L 2300/0645; G01N 15/12; B03C 5/02; B03C 5/005; B03C 5/022; B03C 5/026
USPC ................................ 204/451, 547, 601, 643
See application file for complete search history.

(56) References Cited

U.S. PATENT DOCUMENTS

| | | | |
|---|---|---|---|
| 5,569,591 A | | 10/1996 | Kell et al. |
| 5,580,435 A | | 12/1996 | Kovacs et al. |
| 5,800,690 A | * | 9/1998 | Chow et al. ................. 204/451 |
| 5,810,725 A | | 9/1998 | Sugihara et al. |
| 5,976,336 A | | 11/1999 | Dubrow et al. |
| 6,054,034 A | * | 4/2000 | Soane et al. ................. 204/601 |
| 6,084,503 A | | 7/2000 | Ruile et al. |
| 6,149,789 A | | 11/2000 | Benecke et al. |
| 6,169,394 B1 | | 1/2001 | Frazier et al. |
| 6,482,299 B1 | | 11/2002 | Inganäs et al. |
| 6,521,430 B1 | | 2/2003 | Orwar et al. |
| 6,703,819 B2 | * | 3/2004 | Gascoyne et al. ........... 324/71.4 |
| 6,824,664 B1 | | 11/2004 | Austin et al. |
| 2002/0140414 A1 | | 10/2002 | Sohn et al. |
| 2004/0130338 A1 | | 7/2004 | Wang et al. |
| 2005/0118705 A1 | | 6/2005 | Rabbitt et al. |
| 2006/0081474 A1 | * | 4/2006 | Bryning et al. ............. 204/547 |
| 2006/0169587 A1 | * | 8/2006 | Lopez et al. ................. 204/451 |
| 2009/0104689 A1 | * | 4/2009 | Kim et al. ................. 435/287.1 |

FOREIGN PATENT DOCUMENTS

| | | |
|---|---|---|
| WO | 00/37920 | 6/2000 |
| WO | 02/088321 | 11/2002 |
| WO | WO 03/048728 A2 | 6/2003 |
| WO | WO 2005/089253 A2 | 9/2005 |

OTHER PUBLICATIONS

Ayliffe HE, Frazier AB and Rabbitt RD: 'Electric impedance spectroscopy using microchannels with integrated metal electrodes' *J. Microelectromech. Syst.* 8, 50-57, 1999.
Carbonaro A and Sohn LL: 'A resistive-pulse sensor chip for multianalyte immunoassays' *Lab Chip* 5, 1155-60, 2005.
Chou CF, Tegenfeldt JO, Bakajin O, Chan SS, Cox EC, Darnton N, Duke T and Austin RH: 'Electrodeless dielectrophoresis of single- and double-stranded DNA' *Biophysical Journal* 83, 2170-79, 2002.
Chun HG, Chung TD and Kim HC: 'Cytometry and velocimetry on a microfluidic chip using polyelectrolytic salt bridges' *Analytical Chemistry* 77, 2490-95, 2005.
Cummings EB and Singh AK: 'Dielectrophoresis in microchips containing arrays of insulating posts: Theoretical and experimental results' *Analytical Chemistry* 75, 4724-31, 2003.
Fiedler S, Shirley SG, Schnelle T and Fuhr G: 'Dielectrophoretic sorting of particles and cells in a microsystem' *Analytical Chemistry* 70, 1909-15, 1998.
Gascoyne PRC and Vykoukal J: 'Particle separation by dielectrophoresis' *Electrophoresis* 23, 1973-83, 2002.
Gawad S, Schild L and Renaud P: 'Micromachined impedance spectroscopy flow cytometer for cell analysis and particle sizing' *Lab on a Chip* 1, 76-82, 2001.
Haas K, Sin WC, Javaherian A, Li Z and Cline HT: 'Single-cell electroporation for gene transfer in vivo' *Neuron* 29, 583-91, 2001.
Hagedorn R, Fuhr G, Muller T and Gimsa J: 'Traveling-wave dielectrophoresis of microparticles' *Electrophoresis* 13, 49-54, 1992.
Huang Y and Rubinsky B: 'Micro-electroporation: Improving the efficiency and understanding of electrical permeabilization of cells' *Biomedical Microdevices* 2, 145-50, 1999.
Huang Y, Chen N, Borninski J and Rubinsky B: 'A novel microfluidic cell-chip for single cell analysis and manipulation' *Proc. MEMS* (Kyoto), 403-06, 2003.
Kaler KVIS and Jones TB: 'Dielectrophoretic spectra of single cells determined by feedback-controlled levitation' *Biophysical Journal* 57, 173-82, 1990.
Khine M, Lau A, Ionescu-Zanetti C, Seo J and Lee LP: 'A single cell electroporation chip' *Lab on a Chip* 5, 38-43, 2005.
Koch M, Evans AGR and Brunnschweiler A: 'Design and fabrication of a micromachined Coulter counter' *J. Micromech. Microeng.* 9, 159-61, 1999.
Larsen U, Blankenstein G and Ostergaard S: 'Microchip Coulter particle counter' *Proc. Transducers 97 Chicago*, 1319-22, 1997.
Lundqvist JA, Sahlin F, Aberg MAI, Stromberg A, Eriksson PS and Orwar O: 'Altering the biochemical state of individual cultured cells and organelles with ultramicroelectrodes' *Proceedings of the National Academy of Sciences of the United States of America* 95, 10356-60, 1998.
Masuda S, Washizu M and Kawabata I: 'Movement of blood-cells in liquid by nonuniform traveling field' *Ieee Transactions on Industry Applications* 24, 217-22, 1988.
Muller T, Gradl G, Howitz S, Shirley SG, Schnelle T and Fuhr G: 'A 3-d microelectrode system for handling and caging single cells and particles' *Biosensors & Bioelectronics* 14, 247-56, 1999.
Neumann E, Kakorin S and Toensing K: 'Fundamentals of electroporative delivery of drugs and genes' *Bioelectrochemistry and Bioenergetics* 48, 3-16, 1999.
Nieuwenhuis JH, Kohl F, Bastemeijer J and Vellekoop MJ: 'First particle measurements with an integrated Coulter counter based on 2-dimensional aperture control' *Proc. Transducers 03 Boston*, 296-99, 2003.
Pethig R, Huang Y, Wang XB and Burt JPH: 'Positive and negative dielectrophoretic collection of colloidal particles using interdigitated castellated microelectrodes' *Journal of Physics D—Applied Physics* 25, 881-88, 1992.
Roy A and Apparao A: 'Depth of investigation in direct current methods' *Geophysics* 36, 943, 1971.
Schnelle T, Muller T, Gradl G, Shirley SG and Fuhr G: 'Paired microelectrode system: Dielectrophoretic particle sorting and force calibration' *Journal of Electrostatics* 47, 121-32, 1999.
Seger U, Gawad S, Johann R, Bertsch A and Renaud P: 'Cell immersion and cell dipping in microfluidic devices' *Lab on a Chip* 4, 148-51, 2004.
Voldman J, Gray ML, Toner M and Schmidt MA: 'A microfabrication-based dynamic array cytometer' *Analytical Chemistry* 74, 3984-90, 2002.
Weaver JC and Chizmadzhev YA: 'Theory of electroporation: A review' *Bioelectrochemistry and Bioenergetics* 41, 135-60, 1996.
York T, Sun LL, Gregory C and Hatfield J: 'Silicon-based miniature sensor for electrical tomography' *Sensors and Actuators a-Physical* 110, 213-18, 2004.
European Office Action dated Nov. 18, 2013for applicant's EP Patent Application No. 07 705 760.2 that corresponds to Applicant's PCT/IB2007/050338 filed Feb. 1, 2007.
Huang, Yong, et al., "A Novel Microfluidic Cell-Chip for Single Cell Analysis and Manipulation," Jan. 19, 2003, pp. 403-406, XP010636994.
Communication pursuant to Article 94(3) EPC dated Jun. 14, 2017, issued in European Patent Application No. 07 705 760.2.
International Search Report for PCT/IB2007/050338 dated Sep. 6, 2007.
Written Opinion for PCT/IB2007/050338 dated Sep. 6, 2007.
Mueller et al., "A 3-D Microelectrode System for Handling and Caging Single Cells and Particles", *Biosensors and Bioelectronics*, vol. 14, 1999, pp. 247-256, XP001040743.

(56) References Cited

OTHER PUBLICATIONS

Carbonaro et al., "A resistive-pulse sensor chip for multianalyte immunoassays", *Lab on a Chip, Royal Soc. of Chemistry,* vol. 5, No. 10, 2005, pp. 1155-1160, XP008080706.

* cited by examiner

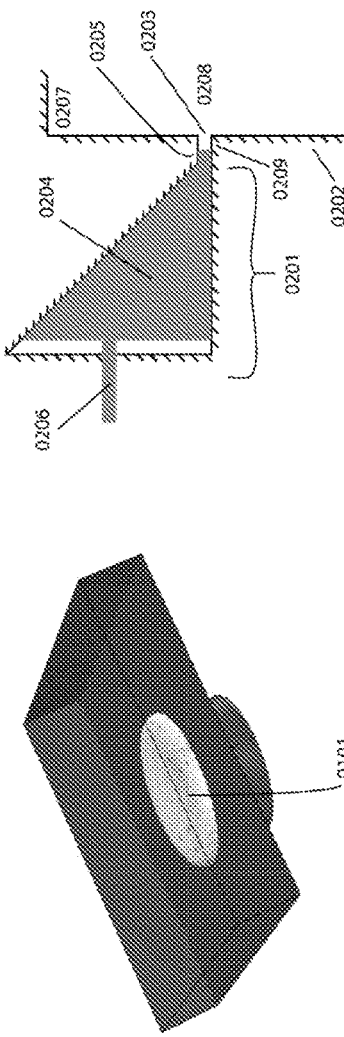
FIG. 1
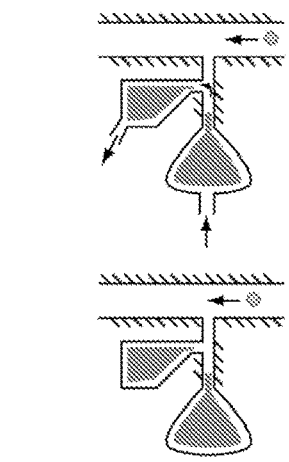
FIG. 2
FIG. 3
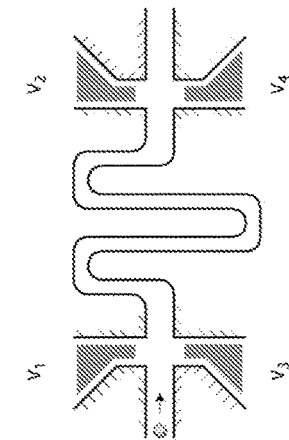
FIG. 4
FIG. 5
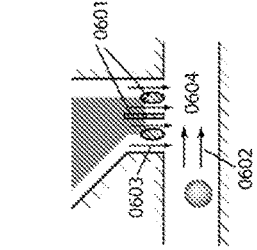
FIG. 6
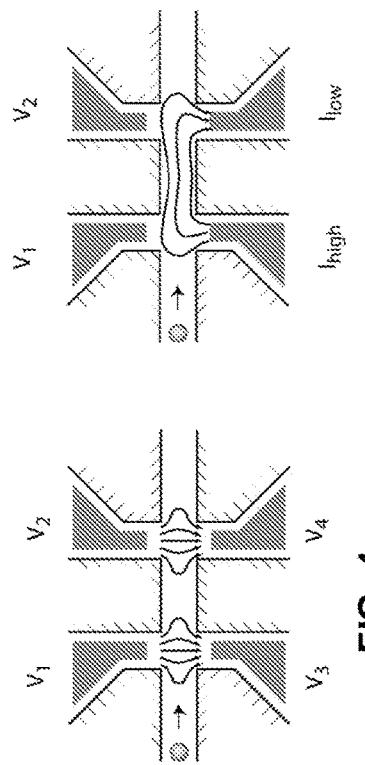
FIG. 7

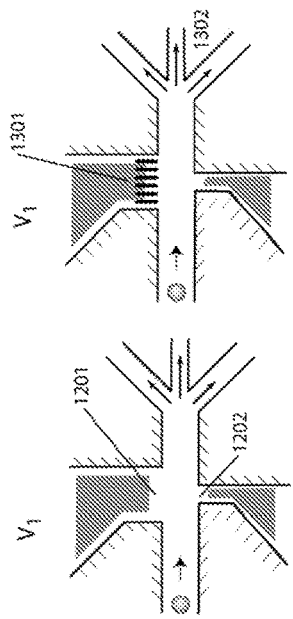
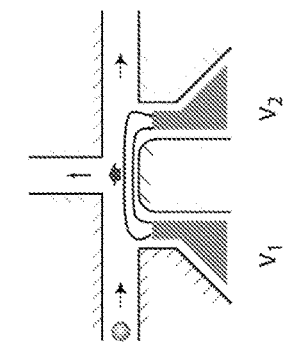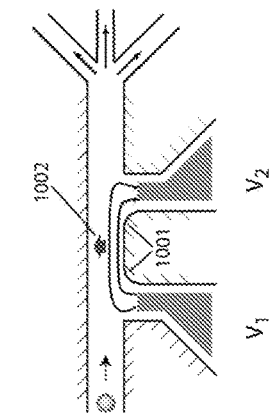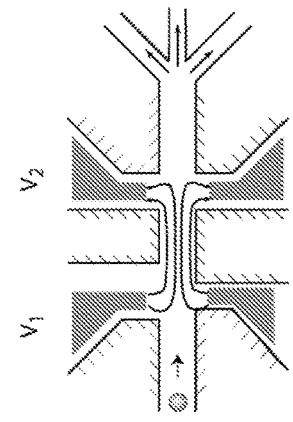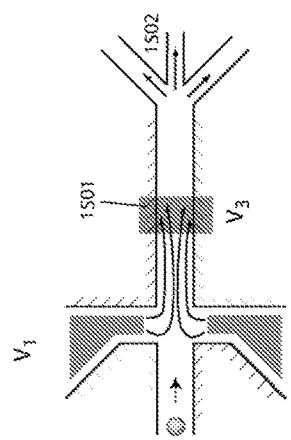

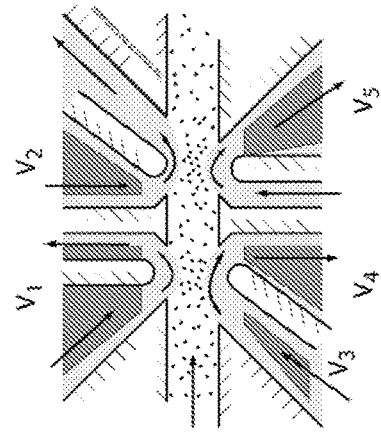
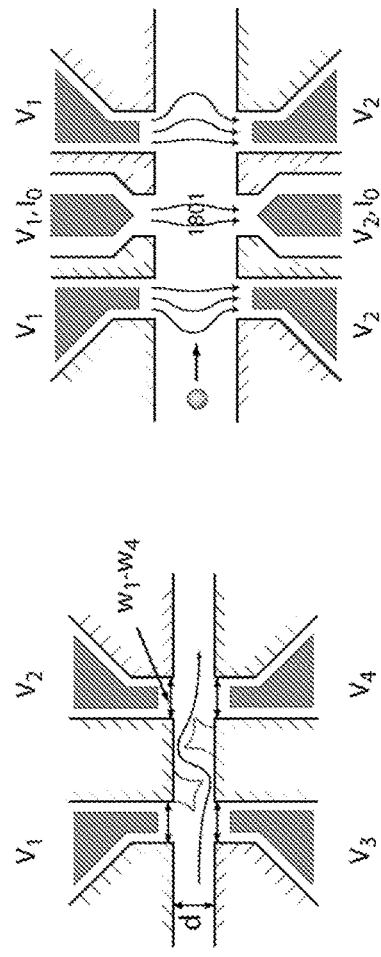
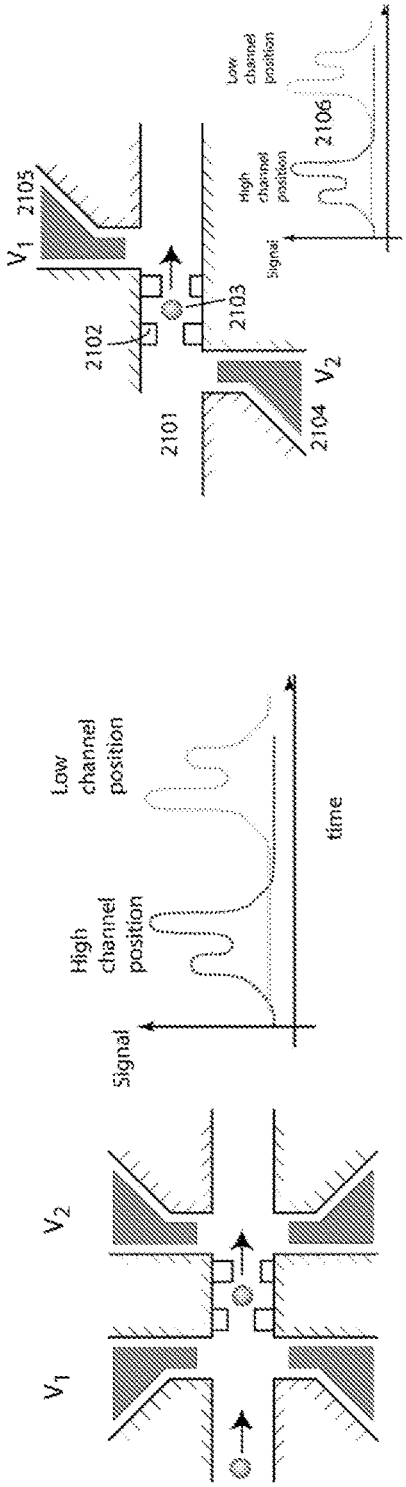

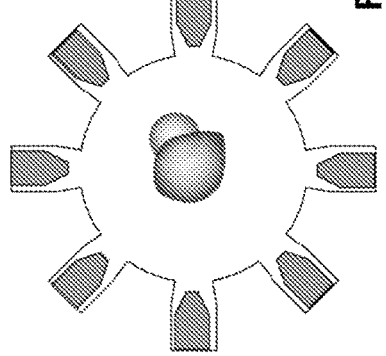
FIG. 28
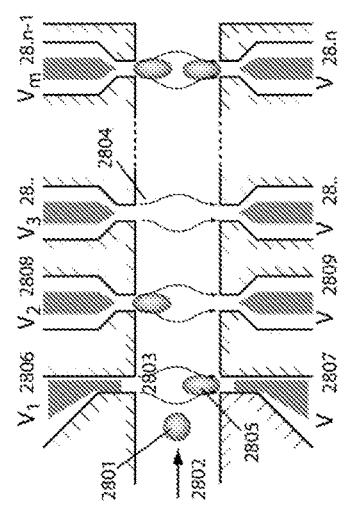
FIG. 29
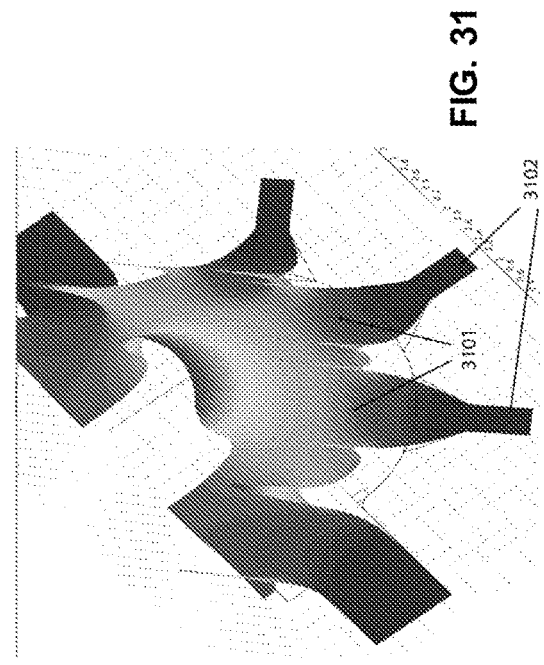
FIG. 30
FIG. 31

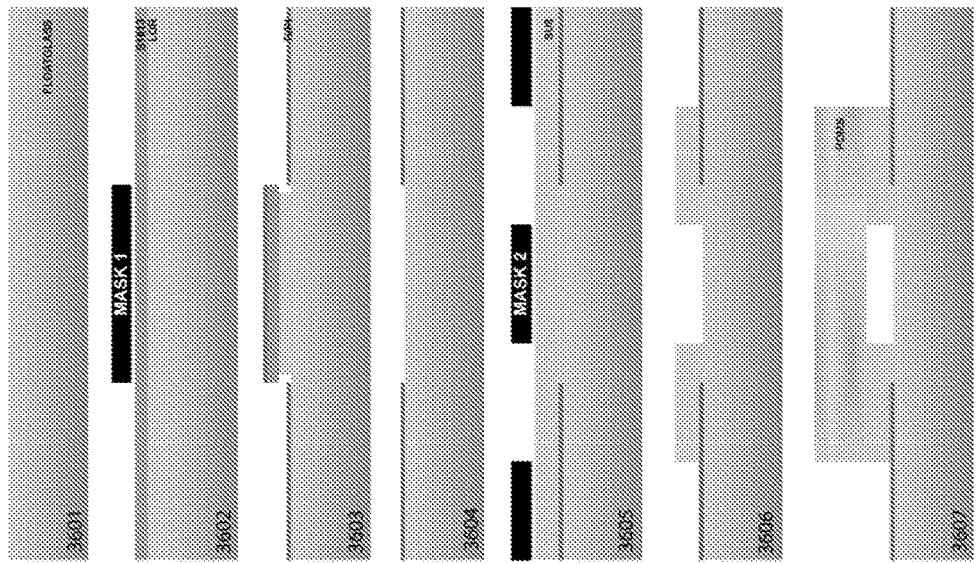
FIG. 36
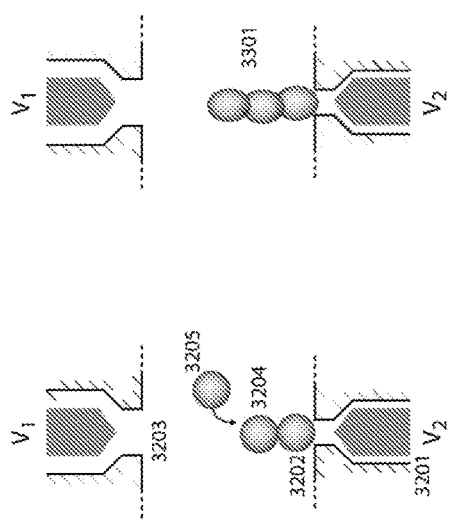
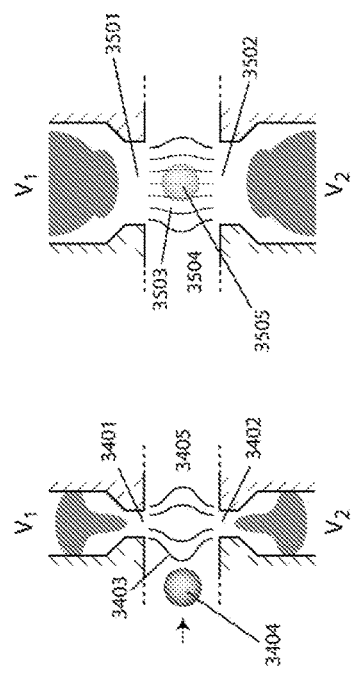
FIG. 33
FIG. 35
FIG. 32
FIG. 34

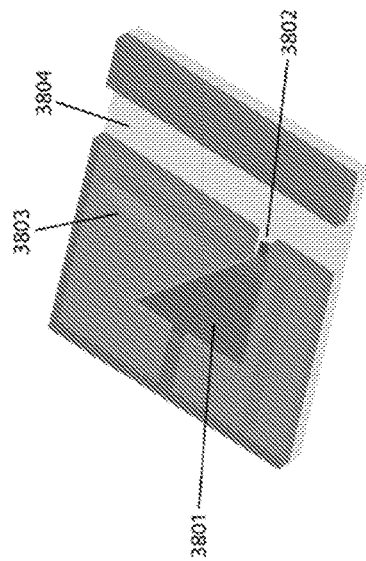
FIG. 38
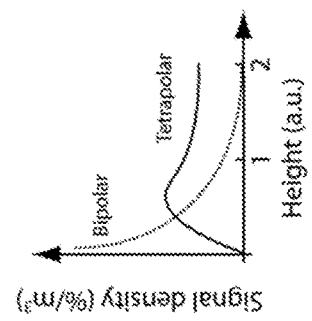
FIG. 39
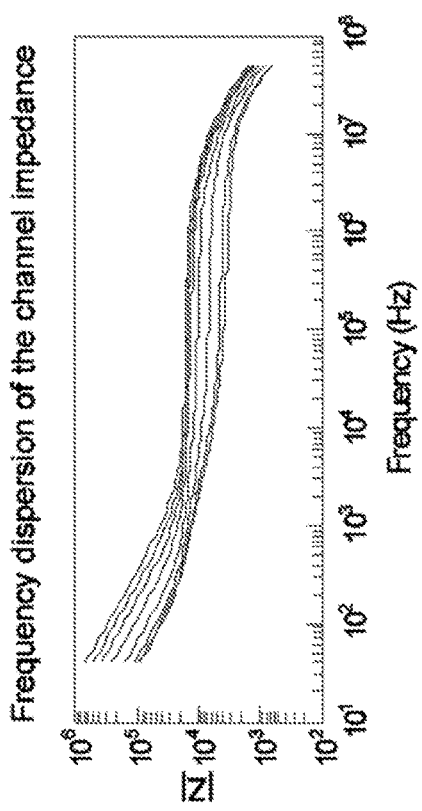
FIG. 37
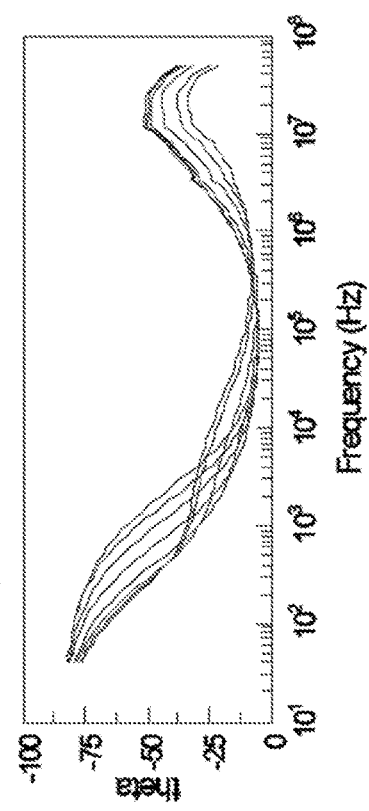

APPARATUS FOR MANIPULATING, MODIFYING AND CHARACTERIZING PARTICLES IN A MICRO CHANNEL

This application is the U.S. national phase of International Application No. PCT/IB2007/050338 filed 1 Feb. 2007 which designated the U.S. and claims priority to International Application No. PCT/IB2006/050345 filed 1 Feb. 2006, the entire contents of each of which are hereby incorporated by reference.

FIELD OF THE INVENTION

The present invention relates in general to the handling, analysis and manipulation of suspended particles by means of electric fields, in particular to current exchange between a microscopic flow channel and macroscopic ohmic contacts and direct applications thereof. Said applications being frequency analysis dependent of the electric response of a particle due to external excitation as well as field gradient-enabled exertion of forces on particles.

STATE-OF-THE-ART

Patent Documents

EP1,335,198, Gawad et al., Mikrofluidisches Bauelement und Verfahren für die Sortierung von Partikeln in einem Fluid.
US 2002/0140414 A1, Sohn et al., Methods and Apparatus for Analysis of Biological Solutions.
US 2004/0130338, Wang et al., Electrical Impedance Tomography.
US 2005/0118705 A1, Rabbitt et al., Electrical Detectors for Microanalysis.
U.S. Pat. No. 5,569,591, Kell et al., Analytical or Monitoring Apparatus and Method.
U.S. Pat. No. 5,580,435, Kovacs et al., System for Detecting Components of a Sample in Electrophoretic Separation.
U.S. Pat. No. 5,810,725, Sugihara et al., Planar Electrode.
U.S. Pat. No. 6,084,503 Ruile et al, Radio-Interrogated Surface-Wave Technology Sensor.
U.S. Pat. No. 6,149,789, Benecke et al., Process for Manipulating Microscopic, Dielectric Particles and a Device therefore.
U.S. Pat. No. 6,169,394 B1, Frazier et al., Electrical Detector for Micro-Analysis Systems.
U.S. Pat. No. 6,482,299 B1, Inganäs et al., Polymer Gel Electrode.
U.S. Pat. No. 6,521,430, Orwar et al., Method for Electropermeabilization of Individual Cellular and Organellar Structures and Use thereof.
U.S. Pat. No. 6,824,664 B1, Austin et al., Electrode-less Dielectrophoresis for Polarizable Particles.
WO 03/048728 A2, Gascoyne et al., Particle Impedance Sensor.
WO 2005/089253 A2, Lee et al., Methods and Apparatus for Integrated Cell Handling and Measurements.
WO 99/52340, Fuhr et al., Method and Device for Manipulating Microparticles in Fluid Flows.

Other Publications

Arnold W M, Schwan H P and Zimmermann U: 'Surface conductance and other properties of latex-particles measured by electrorotation' *Journal of Physical Chemistry* 91, 5093-98, 1987.
Ayliffe H E, Frazier A B and Rabbitt R D: 'Electric impedance spectroscopy using microchannels with integrated metal electrodes' *J. Microelectromech. Syst.* 8, 50-57, 1999.
Carbonara A and Sohn L L: 'A resistive-pulse sensor chip for multianalyte immunoassays' *Lab Chip* 5, 1055-60, 2005.
Chou C F, Tegenfeldt J O, Bakajin O, Chan S S, Cox E C, Darnton N, Duke T and Austin R H: 'Electrodeless dielectrophoresis of single- and double-stranded DNA' *Biophysical Journal* 83, 2170-79, 2002.
Chou C F, Tegenfeldt J O, Bakajin O, Chan S S, Cox E C, Darnton N, Duke T and Austin R H: 'Electrodeless dielectrophoresis of single- and double-stranded DNA' *Biophysical Journal* 83, 2170-79, 2002.
Chun H G, Chung T D and Kim H C: 'Cytometry and velocimetry on a microfluidic chip using polyelectrolytic salt bridges' *Analytical Chemistry* 77, 2490-95, 2005.
Cummings E B and Singh A K: 'Dielectrophoresis in microchips containing arrays of insulating posts: Theoretical and experimental results' *Analytical Chemistry* 75, 4724-31, 2003.
Fiedler S, Shirley S G, Schnelle T and Fuhr G: 'Dielectrophoretic sorting of particles and cells in a microsystem' *Analytical Chemistry* 70, 1909-15, 1998.
Gascoyne P R C and Vykoukal J: 'Particle separation by dielectrophoresis' *Electrophoresis* 23, 1973-83, 2002.
Gawad S, Schild L and Renaud P: 'Micromachined impedance spectroscopy flow cytometer for cell analysis and particle sizing' *Lab on a Chip* 1, 76-82, 2001.
Haas K, Sin W C, Javaherian A, Li Z and Cline H T: 'Single-cell electroporation for gene transfer in vivo' *Neuron* 29, 583-91, 2001.
Hagedorn R, Fuhr G, Muller T and Gimsa J: 'Traveling-wave dielectrophoresis of microparticles' *Electrophoresis* 13, 49-54, 1992.
Huang Y and Rubinsky B: 'Micro-electroporation: Improving the efficiency and understanding of electrical permeabilization of cells' *Biomedical Microdevices* 2, 145-50, 1999.
Huang Y, Chen N, Borninski J and Rubinsky B: 'A novel microfluidic cell-chip for single cell analysis and manipulation' Proc. MEMS (Kyoto), 403-06, 2003.
IEEE EMB: 'Micro medicine—sorting cells and finding bugs with micro- and nanoelectrokinetics' *Ieee Engineering in Medicine and Biology Magazine* 22, 1-128, 2003.
Jones T B: 'Electromechanics of particles' *Cambridge University Press (Cambridge)*, 1995.
Kaler K V I S and Jones T B: 'Dielectrophoretic spectra of single cells determined by feedback-controlled levitation' *Biophysical Journal* 57, 173-82, 1990.
Khine M, Lau A, Ionescu-Zanetti C, Seo J and Lee L P: 'A single cell electroporation chip' *Lab on a Chip* 5, 38-43, 2005.
Koch M, Evans A G R and Brunnschweiler A: 'Design and fabrication of a micromachined Coulter counter' *J. Micromech. Microeng.* 9, 159-61, 1999.
Larsen U, Blankenstein G and Ostergaard S: 'Microchip Coulter particle counter' *Proc. Transducers 97 Chicago*, 1319-22, 1997.
Lundqvist J A, Sahlin F, Aberg M A I, Stromberg A, Eriksson P S and Orwar O: 'Altering the biochemical state of individual cultured cells and organelles with ultramicroelectrodes' *Proceedings of the National Academy of Sciences of the United States of America* 95, 10356-60, 1998.
Masuda S, Washizu M and Kawabata I: 'Movement of blood-cells in liquid by nonuniform traveling field' *Ieee Transactions on Industry Applications* 24, 217-22, 1988.

Morgan H and Green N G: 'Ac electrokinetics—colloids and nanoparticles' *Research Studies Press (Hertfordshire)*, 2003.

Muller T, Gradl G, Howitz S, Shirley S G, Schnelle T and Fuhr G: 'A 3-d microelectrode system for handling and caging single cells and particles' *Biosensors & Bioelectronics* 14, 247-56, 1999.

Neumann E, Kakorin S and Toensing K: 'Fundamentals of electroporative delivery of drugs and genes' *Bioelectrochemistry and Bioenergetics* 48, 3-16, 1999.

Nieuwenhuis J H, Kohl F, Bastemeijer J and Vellekoop M J: 'First particle measurements with an integrated Coulter counter based on 2-dimensional aperture control' *Proc. Transducers* 03 Boston, 296-99, 2003

Pethig R, Huang Y, Wang X B and Burt J P H: 'Positive and negative dielectrophoretic collection of colloidal particles using interdigitated castellated microelectrodes' *Journal of Physics D-Applied Physics* 25, 881-88, 1992.

Pohl H A: 'Dielectrophoresis: The behavior of neutral matter in nonuniform electric fields' *Cambridge University Press (Cambridge)*, 1978.

Roy A and Apparao A: 'Depth of investigation in direct current methods' *Geophysics* 36, 943, 1971.

Schnelle T, Muller T, Gradl G, Shirley S G and Fuhr G: 'Paired microelectrode system: Dielectrophoretic particle sorting and force calibration' *Journal of Electrostatics* 47, 121-32, 1999.

Seger U, Gawad S, Johann R, Bertsch A and Renaud P: 'Cell immersion and cell dipping in microfluidic devices' *Lab on a Chip* 4, 148-51, 2004.

Voldman J, Gray M L, Toner M and Schmidt M A: 'A microfabrication-based dynamic array cytometer' *Analytical Chemistry* 74, 3984-90, 2002.

Weaver J C and Chizmadzhev Y A: 'Theory of electroporation: A review' *Bioelectrochemistry and Bioenergetics* 41, 135-60, 1996.

York T, Sun L L, Gregory C and Hatfield J: 'Silicon-based miniature sensor for electrical tomography' *Sensors and Actuators a-Physical* 110, 213-18, 2004.

Zimmermann U: 'Electrical breakdown, electropermeabilization and electrofusion' *Reviews of Physiology Biochemistry and Pharmacology* 105, 175-256, 1986.

The use of electric fields for measurement, handling and manipulation of particles is widespread in the Microsystems technologies. Depending on the application, either highly homogeneous (e.g. analysis) or highly fringing (e.g. manipulation) fields are used. The shape of the electric field is controlled by the shape and the arrangement of the electrodes in the microchannel.

Typical applications of electric field injection and retrieval encompass (di)electric cell characterization (bipolar/tetrapolar impedance), dielectrophoretic cell handling (deviation, separation, trapping), electric cell manipulation (electroporation, electrofusion) and secondary characterization (electrorotation, levitation, deformation).

Technology-wise, two main directions can be distinguished: large-scale repetitive field topologies are defined by planar 2D electrode or field restriction patterns that are controlled in groups; or punctual field topologies, obtained by individually addressable electrode strips in more complicated fluidic channel structures and/or 3-dimensional arrangements. The most sophisticated devices in terms of fabrication feature electrodes in sidewalls or electrode patterns on aligned top-bottom substrates.

Solid-State Microelectrodes

Microelectrodes made out of metal are ubiquitous in microsystems. They are used to measure changes in potential, injecting current as guarding systems or to provide a floating potential in a part of the system.

These electrodes are typically made out of a metal patch which is patterned using photolithography onto an insulating substrate such as glass or silicon. In microfluidic applications, a system of channels is then created around the electrodes, for example by patterning of a thick photoresist such as polyimide or SU8, or by sandwiching the system with another part having channels.

U.S. Pat. No. 6,482,299 B 1, which is hereby incorporated by reference, discloses a polymer gel electrode which has a high conductivity and a very porous surface. Electrodes made from organic conductors can have a very low interfacial capacitance, but the surface is often not reproducible, and they do only lower the impedance an order of magnitude.

U.S. Pat. No. 5,810,725, which is hereby incorporated by reference, discloses a method for improving the charge transfer properties for microelectrodes by engineering the material choice.

An important limitation of metal microelectrodes is that they exhibit a very high impedance, often referred to as the "double-layer capacitance", at low frequencies. The physical background to this phenomenon is the solid-liquid interface between electronic and ionic conduction for the current. Since the interface impedance is inversely related to the surface area of the electrode, microelectrodes in general have a very high impedance (M$\Omega$) at low frequencies (<1 kHz). Furthermore, metallic microelectrodes also frequently have only a limited life-time, since the metal slowly corrodes. Other limitations of microstructured metal electrodes in contact with liquid in a channel are the following: Extreme current densities appearing at electrode edges might lead to chemical reactions and thus harm biological particles in proximity or even degrade the electrodes. The presence of conducting coatings placed in external electric fields leads to alteration of the external field at high frequencies due to coupling into and out of the metal patch. Variations in flow speed above the electrodes result in changed electric behaviour due to thermal or ionic evacuation or supply.

US 2005/0118705, which is hereby incorporated by reference, discloses a method/process for measuring electrical properties through an aperture in a microchannel. However, the use of a metal electrode patterned in the microchannel will introduce an important perturbation of the electric field. Furthermore, the metal patch responsible for current injection is too small to significantly reduce the effect of the double layer, and the same patch is placed far away from the tapered section of the auxiliary channel, increasing the access resistance considerably.

If the abovementioned limitations of metal electrodes can be overcome by an alternative approach of measuring the electric potential and injecting/retrieving current into microchannels, devices for manipulation and handling of biological particles could be both cheaper and provide more biologically relevant information.

Impedance Measurements of Cells and Particles

Impedance based sensing is a well-known method for characterizing biological cells and dielectric particles in general. The measurements can be performed either in a flow or for stationary particles positioned at a certain distance from the electrodes. The advantage of impedance measurements compared to fluorescence based techniques is that they are label-free, which reduces the risk of altering the cells and their behaviour. At present, more and more applications in research are geared towards detection and characterization of dielectric particles such as proteins and viruses.

The measurement setup used in impedance measurements can be either bipolar, where the same electrodes are used for both current injection and the potential measurements, or tetrapolar, where two dedicated pick-up electrodes are used to monitor the potential difference between two points, and two injecting electrodes are used to inject the electrical current into the sample. A powerful method in-between is the tripolar method, where two excitation electrodes are driven in counter-phase, and a single pickup electrodes measures the potential midway between the excitation electrodes.

Typical cellular parameters that can be investigated with an impedance based sensor include the membrane capacitance, the cytosol conductivity, the size of the cell, etc. These parameters are extracted from the measurements by fitting the measurements to different models.

The bipolar impedance measurement in a microchannel is usually modelled as a interfacial impedance in series with the impedance of the sample (the sample between the electrodes). These two elements are then short-circuited at high frequencies by the stray capacitances of the measuring circuit, as well as by the capacitive path through the bulk (dipole reorientations). The simplest model of the interfacial impedance is a pure capacitor. A slightly more accurate model is obtained by modelling the interface as a mathematical equation such as a constant-phase element (CPE) or a Warburg impedance. These models are often used for low-amplitude signals, but to take electrochemical reactions into account a more complex circuit is often needed, encompassing an element such as a CPE for the capacitive pathway and a resistor for the resistive pathway in which chemical reactions occur.

These different elements are all affected by the size of the electrode, the material (the charge-transfer capabilities of the solid-state electrode), the surface roughness, etc.

The bulk impedance depends on the material in the channel and its characterization lies at the heart of the diverse impedance measurement methods. The simplest model is a pure resistor, an approximation which is acceptable at low amplitudes and low frequencies. This model can be useful to characterizing insulating particles in a flow-through manner. The change in resistance of the particle passing through the channel is then given by the volume and the conductivity of the particle and the conductivity of the medium.

At higher frequencies the permittivity of the material must be taken into account, which can be done by incorporating one or several capacitors. At high signal strengths non-linear effects such as ion depletion and cell membrane permeabilization must be taken into account in order to accurately model the obtained impedance spectra.

It should be pointed out that regardless of what model is used, the change in impedance produced by a particle is a complex function of the particle shape, its electrical properties and the original electric field. For small perturbations, the sensitivity is proportional to the local power dissipation. It is known that the sensitivity distribution of a bipolar or tetrapolar impedance measurement can be expressed as the vector product of the vector field of the injection electrodes and the pick-up electrodes respectively (Roy A 1971). Mathematically this can be expressed as:

$$S = \vec{J}_1 \cdot \vec{J}_2$$

Where $J_1$ is the field produced by the injecting electrodes and $J_2$ is the field produced by the voltage measuring electrodes. In the bipolar case $J_1=J_2$. The bipolar measurement is therefore always very sensitive to changes occurring at the electrode surface, and in particular at the electrode edges where the field is the strongest.

Several authors have demonstrated successful implementations of impedance measurements of individual suspended particles in microfluidic chips with microelectrodes.

Impedance sensors are also disclosed in U.S. Pat. Nos. 6,169,394, 6,149,789, 6,084,503, 5,580,435 and 5,569,591, each of which is hereby incorporated by reference. The first devices were miniaturized Coulter counters. In these devices, the bipolar measurement field passing in parallel with the cells through the orifice (Larsen U 1997, Koch M 1999).

Nieuwenhuis et al. discloses a method for placing the dielectric particle in an insulating sheath-flow (Nieuwenhuis J H 2003). In this device, the cell is placed in a jet of a highly-conducting medium surrounded by a lowly conducting sheath flow. This allows for a focussing of the electric field and a better signal. The size of the jet can be modulated.

U.S. Pat. No. 6,169,394, which is hereby incorporated by reference, discloses an electrical detector for micro-analysis systems. Frazier et al. describes bipolar on-chip impedance measurements with fields perpendicular to the particle flow direction using lateral solid-state electrodes.

The disadvantages with bipolar measurement using solid-state microelectrodes include a) low-frequency measurements are not possible, or at best extremely noisy b) the measurements are very sensitive to drift.

EP1,335,198, which is hereby incorporated by reference, discloses a process for differential bipolar impedance measurements of biological cells. The invention makes use of two facing pairs of electrodes patterned on top and at the bottom of a microchannel. The invention by Gawad et al. partially reduces the drift, but makes it excruciatingly difficult to extract the absolute electrical values of a passing particle.

WO 03/048728, which is hereby incorporated by reference, discloses a process for impedance measurements of cells using a three-port method with symmetric excitation. In this device, the pick-up electrode is placed midway between two electrodes injecting currents in opposite phase, so that in equilibrium the pick-up is at zero voltage. The passage of a cell causes a symmetric perturbation around zero of the voltage. Like the differential bipolar measurement, the three-port device reduces noise and in particular drift but is still limited by the interfacial impedance of the electrodes.

Devices for tetrapolar impedance measurements have the advantage of being less sensitive to the electrode fouling and electrochemical reactions at the electrode surface. Furthermore, it is known that the maximum sensitivity for a bipolar measurement is at the electrode surface, but the sensitivity for a four-point measurement can be greater at a certain distance into the sample (FIG. 39). The disadvantage with the tetrapolar measurements is that the potential difference is smaller between the pick-up electrodes, regardless where they are placed, than between the two current injecting electrodes, which makes common mode rejection in the detection electronics more critical.

Like in the bipolar case, the electric field in the tetrapolar case can be parallel or perpendicular to the liquid flow.

US 2005/0118705, which is hereby incorporated by reference, discloses a process for tetrapolar impedance measurements using an electric field parallel to the microfluidic channel. The parallel fields are created by microelectrodes patterned at the bottom of the main channel, and the pick-up electrodes are patterned between the injection electrodes. There are several drawbacks with this arrangement; the detection zone is about as wide as the distance between the edges of the injection electrodes, the solid-state microelectrodes are not suitable for pick-up electrodes since they require an extremely high input impedance in the apparatus measuring the potential, and the presence of metal in the microchannel distorts the electric fields.

The tetrapolar devices built using electric fields perpendicular to the main channel may alleviate some of these problems (Huang Y 2003). In these devices, the electrodes have been patterned in an auxiliary channel perpendicular to the main channel. The detection zone is still wide, but since the particles are confined to the microchannel, the effective detection volume is confined to the cross section of the auxiliary channel and the main channel.

Tetrapolar measurements can also be carried out using large number of electrodes where the electrodes are alternatively used for current injection and voltage pick-up. This has been used in medicine to make images under the name "impedance tomography", and in geophysics under the name "resistivity imaging", which has been used to study glaciers, ground composition, etc.

York et al. presented a technique for creating images of small particles inside a cylindrical apertures (York T 2004). They used a 16 electrode array where the electrodes were made by electroplated copper.

US 2004/0130338, which is hereby incorporated by reference, discloses a method for imaging particles and mixed flow patterns in a tube.

Electrokinetic Manipulation of Particles

One fundamental interaction occurring under specific conditions is dielectrophoresis (DEP). Dielectrophoresis is an electrical force that can interact with dielectric particles by induction of charge displacements (Pohl H A 1978, Jones T B 1995). An inhomogeneous alternative electric field in a dielectric medium is required for building a dielectrophoretic potential. The magnitude of the dielectrophoresis depends on dielectric properties of the medium relatively to the dielectric properties of particles and is proportional to the gradient of the electric field intensity. Depending on the dielectric properties of particles and surrounding medium, these forces are directed towards or away from dense electric fields. This frequency-dependent behaviour is termed positive or negative dielectrophoresis (pDEP or nDEP), respectively.

In the case of alternating fields, the time averaged dielectrophoretic net force on a lossy, spherical particle is given by $$\vec{F}_{DEP} = 2\pi\varepsilon_l R^3 \cdot \Re\left(\frac{\varepsilon_p - \varepsilon_l}{\varepsilon_p + 2\varepsilon_l}\right) \cdot \vec{\nabla} E_{rms}^2$$

where $\varepsilon_l$ is the permittivity of the medium, R the radius of the spherical particle and $\nabla E_{rms}^2$ the gradient of the square of the effective electric field. The character $\Re$ designates the real part of the quotient in parentheses, called Clausius-Mossotti (CM) factor: it expresses the polarizability of the particle, i.e. its ability to become dipolar. The CM factor depends on the frequency via the complex permittivities of the suspension liquid $\varepsilon_l$ and of the particle $\varepsilon_p$.

Progress in microfabrication has lead to a number of direct applications of dielectrophoresis (Morgan H 2003, IEEE EMB 2003).

Planar interdigitated or intercastellated electrode patterns allow for particles populations separation enabled by p/nDEP crossover frequencies (Pethig R 1992; Gascoyne PRC 2002).

Three- or more phase driven electrode grids yield twDEP—travelling wave dielectrophoresis (Masuda S 1988; Hagedorn R 1992).

Long-term trapping of biological cells is preferentially done with negative dielectrophoresis as the cells reside at zones with low field intensity; typical trapping structures are field bottles or octocages between top-bottom patterned electrode structures (Muller T 1999) or extruded pillars traps (Voldman J 2002). Paired microelectrode strips (Schnelle T 1999) can be used for passive (Fiedler S 1998) and active (Gawad S 2001) cell sorting, of for guiding particles from one liquid to another (WO 99/52340; Seger U 2004).

Short-term trapping or concentration of biological and other matter can be achieved by pDEP: polarizable particles are attracted along the field gradient towards the most dense fields with appear either at electrode edges and tips (Pethig R 1992), or within structures concentrating external fields via insulating restrictions (electrodeless DEP) and obstacles (Chou C F 2002; Cummings E B 2003; U.S. Pat. No. 6,824,664 B1).

Individual dielectric particle characterization can be achieved by levitation experiments (Kaler K V I S 1990) and most accurately by electrorotation (Arnold W M 1987).

Combining pDEP with supplementary chemical and electrical stimuli can result in electrofusion (Zimmermann U 1986).

A research domain on its own is electropermeabilization (EP), strong electric fields can kill cells [lysis]; under optimised conditions, cells can open, reseal and survive [electroporation] (Weaver J C 1996; Neumann E 1999). Several miniaturized or microfabricated EP setups have been presented: In-vitro and in-vivo single cell EP has been achieved by motorized microelectrode tips (Lundqvist J A 1998) or micropipettes (Haas K 2001). Planar and top-bottom electrode patterns in microchannels have been successfully used for electrical cell lysis or electroporation. Alternatively to field enhancement by electrode size reduction, integrated EP devices based on field concentration have been introduced by the groups of Rubinsky (Huang Y 1999) [vertical, silicon] and of Lee (Khine M 2005) [lateral, silicone].

The problem with all the above-mentioned devices featuring solid-state electrodes is that they are limited by the electrode capacitance and important local heating at the electrode edges, which also might disturb the flow pattern in the microchannel.

SUMMARY OF THE INVENTION

The present invention relates to a fluidic system comprising a space for containing a liquid and at least one lateral chamber in communication with said space, said lateral chamber containing an electrode, wherein said lateral chamber and said space are designed to be filled with liquid when the system is active.

In the present invention, the solid-liquid interface of traditional metal electrodes adjacent to a micro channel or other cavity is replaced by the continuous liquid interface between the main channel, or more generally, the working zone, and a lateral chamber. This so-called liquid electrode may be used to probe, measure or manipulate cells in the working zone, as it is capable of injecting and picking up currents into and from the latter. By varying design parameters of the elements necessary to create a liquid electrode, the electric field at its interface with the working zone can be precisely engineered. The liquid electrode chamber is made up of a metal patch (with an ohmic connection to the measurement instrumentation). The liquid in the chamber can be filled either by gas evacuation through the lid, or through the use of a separate liquid handling system. The metal patches conform to the form of the liquid electrode chamber, in order to reduce the access resistance. An electric field can be established inside the structure (consisting in at least two liquid electrodes and a working zone) by applying a potential difference between two different liquid electrodes. This results in a flux of ions flowing from a liquid electrode, through the working zone, toward another liquid electrode.

The chemical (composition) and electrical (frequency response, local and total current density, etc.) properties of the liquid electrode can be tailored by the geometry of the structured chamber behind (shape and height of the chamber, shape of the metal patch, chemical and electrical properties of the fluid). It is important to note that the electric field at the liquid electrode surface not only depends on the shape of the aperture, but also on the geometry of the liquid electrode channel, the electrical properties of the liquid filling and the metal electrode, etc. The liquid electrodes can also be connected to a separate flow system which will hinder contamination of the electrodes due to diffusion, as well as enabling more types of measurements and sample manipulations. Dynamic liquid electrodes give rise to extremely versatile modular current isolation, injection or pickup geometries, optionally combined with the supply or retrieval of chemical reagents.

One liquid electrode has one of the following electrical functions: voltage measurement or current injection.

An invention for impedance measurements is also presented. Using two lateral current injection electrodes, and two facing voltage pick-up electrodes, a four-point measurement can be performed of the substance between the electrodes, yielding a measurement with an excellent signal-to-noise ratio and homogeneity of the sensitivity in the working zone as well as the possibility of performing low-frequency measurements.

Further invention lies in the new concepts of electrokinetic particle handling using lateral field injection. Different electric field distribution schemes applicable for lateral negative or positive dielectrophoresis are presented. Lateral DEP is particularly suited for particle positioning in the xy plane and can be combined with particle rotation and particle deformation and with particle modification like lysis and electroporation.

A number of other currently existing microelectrode devices can benefit from a substitution of the metal electrode to a liquid electrode. In many cases, the measurement and manipulation concepts can be kept unchanged, and only the channel geometry adapted.

BRIEF DESCRIPTION OF THE FIGURES

FIG. 1
The liquid electrode. A liquid electrode is the equipotential surface (0101) spanning an opening in the wall of a channel (or more generally, the working area). Its properties, such as shape, current-density, potential and frequency dependent characteristics are primarily determined by the chamber behind it, which is equipped with a metal microelectrode and filled with a conductive liquid.

FIG. 2
Top view of a typical embodiment of a liquid electrode. On the floor (and possibly the ceiling and the side walls) of a liquid-filled microchamber (0201) a metal (or polymer) solid state electrode is patterned. It has a connection (0206) to a measurement instrument or a supply of voltage or current. The chamber is connected to a working area (0208) by an opening (0203) in the side wall (0202). This opening represents the actual liquid electrode.

FIG. 3
Branched structures. Liquid electrodes may not only open directly into the main working area, but also into the access channels of other liquid electrodes. This creates the possibility of injecting a given electrical quantity such as a potential or current, and to monitor this quantity or some other quantity for the same point in the main working area.

FIG. 4
Bipolar measurements using liquid electrodes. In a bipolar measurement, a given potential difference is imposed across a pair of electrodes (such as V1 to V3 across the corresponding electrodes), and the corresponding current is measured. The measurement region is indicated by the field lines, if a dielectric particle crosses this zone, the current changes according to the dielectric properties of the particle. In order to correct for drift, a second pair of electrodes (V2, V4) can be used and the two current signals subtracted.

FIG. 5
Tetrapolar measurement using liquid electrodes. A given current signal is imposed across the electrode pair Ihigh to Ilow (alternatively, a potential can be imposed and the current measured). Simultaneously, the potentials V1 and V2 are measured by pickup liquid electrodes. Impedance is determined as the ratio between the voltage drop from V1 to V2 as compared to the current flowing through the structure, as measured at Ilow. The measurement can be flow-through, stopped flow or with some particle immobilization technique such as optical traps, hydrogel formation or other.

FIG. 6
Liquid electrode with minimal flow disturbance. Rod shaped small obstacles (0603) are used to minimize flow in the entry region of the liquid electrode while increasing the access impedance of the liquid electrodes only marginally, because the electrical field lines (0601) follow the rods.

FIG. 7
Measurement device with an extended central region. The central region can be extended, allowing for a larger time difference between bipolar measurements (V1 to V3, then V2 to V4) to monitor slower changes in the particle properties, or a longer-term continuous monitoring of the particle in the central part using a tetrapolar measurement setup.

FIG. 10

Figure 9:
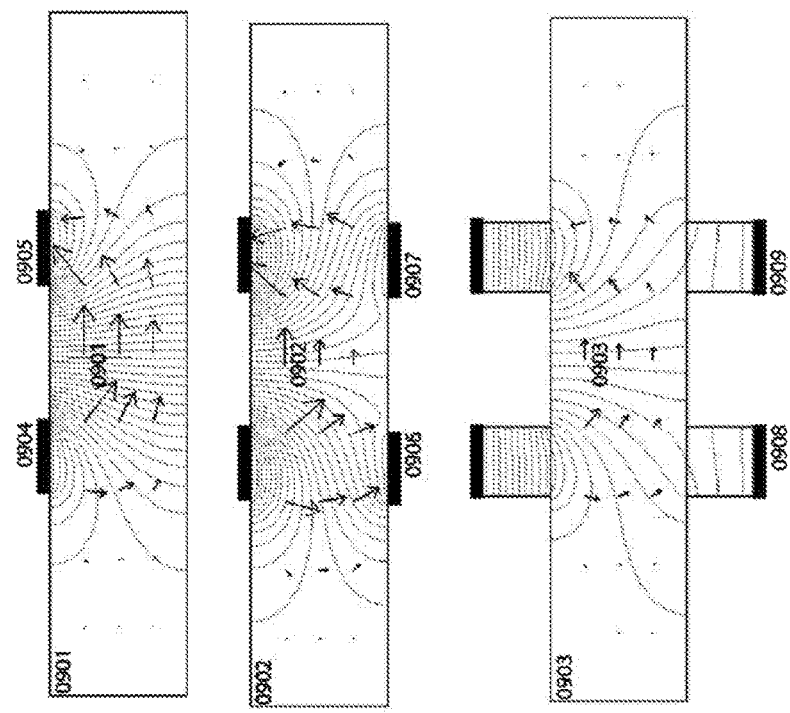
FIG. 9
Disturbance of the electrical field by classical microelectrodes as compared to liquid electrodes as simulated by the finite element method (FEMLAB) in a geometry with facing electrodes. As in FIG. 8, adding measurement electrodes disturbs the original field, but with liquid electrodes, this effect is greatly reduced. Moreover, the field imposed by a pair of liquid electrodes itself is more homogeneous because there are no metal electrode edges in contact with the main channel

Sorting device using nDEP and liquid electrodes. The inhomogeneous field imposed by the two liquid electrodes (V1 and V2) imposes a nDEP force (1002) towards the opposite channel wall. This force can be used to direct particles such as to be dragged into different outlets.

FIG. 11

Sorting device using nDEP and liquid electrodes. The inhomogeneous field imposed by to liquid electrodes can be used to push particles out of the main channel into a branching channel.

FIG. 12

Sorting device using nDEP and facing liquid electrodes. Using two liquid electrodes with openings of different sizes, an asymmetric field can be created and used to push particles such as to be streamed into different outlets

FIG. 13

Sorting device using nDEP and facing liquid electrodes. As in FIG. 12, but field guides are used to optimize the inhomogeneity effect, specifically to avoid undesired nDEP acting on the particle by the fringing of the field into peripheral regions of the main channel

FIG. 14

Sorting device using nDEP from a liquid and a metal electrode in the main channel. The field inhomogeneity caused by the fringing of the field into the entry of the branching channel is used to push particles into the branching channel

FIG. 15

Focusing device using two liquid electrodes and a metal electrode in the main channel. The field is lowest in the midline of the channel when the potentials V1 and V2 are equal, focusing particles to the midline. The field concentration at the metal electrode levitates particles after being focused, avoiding sedimentation. If V1 and V2 are not equal, focusing can be adjusted to any line in the main channel.

FIG. 16

Focusing device using four liquid electrodes. If V1=V3 and V2=V4, focusing to the center line of the channel is achieved by nDEP. If V1>V3>V2>V4, focusing to the upper part of the channel takes place, and if V3>V1>V4>V2, focusing to the lower part of the channel is observed. Detailed analysis shows that focusing to oblique lines as well as into the electrode chambers can be obtained using suitable potentials, which makes the device very versatile.

FIG. 17

Tetrapolar impedance measurements with modified middle channel. Impedance characteristics of cells and particles in general depend on both the particle itself as well as the channel geometry because the current pathways across and around the particle are in competition. By placing obstacles in the central channel part, the particle environment is modified along its path, allowing for repeated measurements with constant particle properties but changing environment impedance characteristics. This may facilitate the extraction of impedance properties specific to the particle, especially for a measurement at a given frequency.

FIG. 18

Liquid electrode guards. By imposing the same potential to guard electrodes (the outer electrodes) as to measurement electrodes (the inner pair), fringing of the field is prevented. This allows for measurement in a more restricted measurement zone, improving signal to noise ratio.

FIG. 19

Dynamic liquid electrodes (DLE). Dynamic liquid electrodes are connected to their own liquid supply system. By imposing flow inside the liquid electrodes chambers, the composition of the liquid can be held permanently different from the one in the main channel, because the flow opposes diffusion. Generally high conductivities will be sought for the liquid in the DLE, and physiological or low conductivity buffers will be used for the main channel containing cells or particles. Several modes are possible: The metal electrode path may span both inlet and outlet (case for V1) for the liquid electrode, only the inlet (case V2) or only the outlet (case V5). Alternatively, distinct metal electrodes may be placed in both inlet and outlet chamber; they can then be connected to either the same or different potentials or serve to measure current (case V3, V4). The different possibilities can then be assembled to form bi-, tri- or tetrapolar measurements. This figure is an overview, more detailed description of individual configurations and applications can be found in FIGS. 40, 41, 42 and 43. Other than maintaining permanently different compositions in the DLE as compared to the main channel, the supplementary liquid supply can be used to perform additional functions such as hydrodynamic focusing or delivery of pharmacological reagents as well as pickup of metabolites in the main stream via diffusion or deliberate aspiration.

FIG. 20

Lateral position detection using a tetrapolar measurement. The sensitivity of impedance measurements is not homogeneous across the main channel, and this can be used to detect lateral position. In the tetrapolar configuration shown the asymmetry of the obstacles in the measurement portion of the channels leads to increased sensitivity in upper part for the first obstacle pair, and the lower part of the opening for the second obstacle pair. The peak for particles passing with high or low trajectories are thus different, as shown in the inset. This allows for detection, and subsequently for correction for the lateral position.

FIG. 21

Lateral position detection using a bipolar measurement. As in FIG. 20, the sensitivity is not homogeneous across the measurement channel, it is higher at the lower portion in the first part, and higher towards the upper part at the second obstacle. Thus lateral position detection is again possible comparing the peak heights at the two obstacles.

FIG. 22 nDEP field cage. Imposing two voltages (V1 and V2) to liquid electrodes as shown in the figure leads to a field minimum at the centre of the structure. Under nDEP conditions, this field cage allows trapping of a particle such as a cell.

FIG. 23

Multi-sorter using nDEP. The main liquid flow is from the inlet to the outlet, with very little flow running to each of the branching channels. This signifies that without an electrical field, particles will go straight from the inlet to the outlet. When the field is switched on from V1 to V2, due to fringing into the branching channels, particles in front of the branching channel are pushed into the branching channels and then transported away by the flow. The structure can be operated in an active mode, where the electrical field is switched off and on according to measurements made upstream to direct particles into the different outlets, and in a passive mode, with the electrical field constantly switched on. In the passive mode, sorting is achieved because different particles experience different nDEP forces in the same field, such that particles experiencing a strong nDEP force will be directed into the first outlets, and particles experiencing a weak nDEP force into outlets located more downstream. In the passive mode, slow flow in the branching channels may be directed towards the outlets as shown in the figure, or in the opposite direction. The case shown in the figure leads to continuous transport of the particles towards the outlet, the opposite flow leads to accumulation and thus concentration of particles at the junctions.

FIG. 24

Cell caging and impedance measurement. A cell may be immobilized by aspiration, or by an nDEP field as shown in the figure against a small opening in the side wall (2402). Impedance can then be measured in a volume including the cell. Several configurations are possible: Measurement from V1 to V2, or V1 to V3, or V2 to V3, or V1 and V2 connected together to V3. Optionally, instead of a single aspiration channel there may be a microfluidic network behind the cell (not shown in figure), allowing for rapid exchange of the liquid and thus for rapid pharmacological stimulation of the cell with continuous impedance monitoring.

FIG. 25

Electroration using liquid electrodes. By driving the pair V1 to V4 at 90° phase offset as compared to V2 to V3, a rotating field is imposed, and this can be used to study electrorotation of the cell at frequencies ranging from the Hz range to GHz.

FIG. 26

Liquid electrode cell dipping. Cells coming from one inlet (2602) are pushed into a liquid stream containing some active reagent (from inlet 2601) by nDEP force from a liquid electrode pair (2606, 2607). In the upper loop (2603) incubation takes place, with the possibility of a liquid electrode impedance measurement or electropermeabilization (electrodes 2613, 2614). After the loop, a second monitoring measurement can be done, alternatively also sorting can be performed using the two electrodes 2609, 2610.

FIG. 27

Electroration with auto focusing. Applying an AC-signal form V2 to V4 and a 90° phase shifted copy of this signal from V1 to V3 leads to a rotating electrical field at the position of the cell or particle (2709). As the field running from V2 to V4 fringes into the openings of the liquid electrodes 2703 and 2706, it shows a minimum at the cell position, centering thus the cell in the horizontal direction. Vice versa, the field running from V1 to V3 fringes into the main channel, creating a minimum in the vertical direction at the position of the cell. Altogether, under nDEP conditions, the cell is not only rotated but cantered in the centre of the structure.

Alternatively, the structure can be used for a combination of electrorotation and impedance measurement. Electrodes 2702, 2704, 2707 and 2705 can be used for electrorotation as described for FIG. 25 with a 90° phase shifted signal. 2703 and 2706 can be used to perform a simultaneous bipolar measurement at a frequency other than the electrorotation frequency or monitor the field during electrorotation. In both cases, orientation dependent information can be acquired. It is also possible to stop electrorotation after a given period and to acquire a tetrapolar measurement using electrodes 2702, 2705, 2707 and 2705, restart electrorotation and so forth.

FIG. 28

Cell capture and electrodeformation using pDEP. The cells or particles are attracted towards the field concentration at the entry region of the liquid electrodes. This allows for immobilization without direct contact to the electrodes, and for patch-clamp like measurements of trans-membrane currents of the immobilized cells. The cells will also deform in the electric field, allowing studying mechanical characteristics such as cytoskeleton response to stretching. Using two facing electrodes, cells can be aligned and fused by electrofusion.

FIG. 29

Impedance tomography using liquid electrodes. A circular arrangement of liquid electrodes is used to measure impedance across a cell (or particle, or cell group, or particle group) in different directions. In this way, anisotropy in the impedance characteristics, such as anisotropic membrane poration by electroporation or mitotic spindle orientation, can be detected.

FIG. 30

Finite element (FEMLAB) simulation of the field intensity in FIG. 16. The x-y plane is the plane of the chip, the z-coordinate represents the square of the magnitude of the electrical field. This simulation shows a valley in the middle of the main channel, meaning that under nDEP conditions focusing is toward the midline of the main channel, while under pDEP conditions, cells will be attracted to the openings of the electrodes.

FIG. 31

Figure 23:
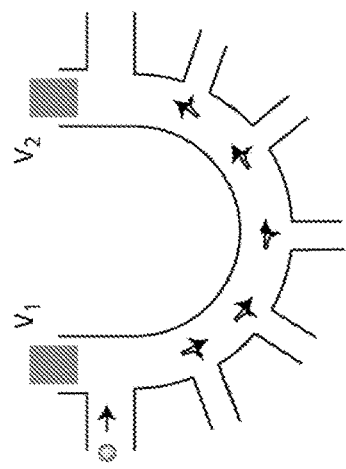

Finite element (FEMLAB) simulation of the field intensity in FIG. 23. The x-y plane is the plane of the chip, the z-coordinate represents the square of the magnitude of the electrical field. Field minima are in the branching channels, field maxima towards the inner wall of the half-circle, as well as at the corners near the branching channels. Note that in this structure, field minima are never at the wall, meaning that under nDEP conditions cells will never be pushed into the wall by the electric field but always held at a certain distance.

FIG. 32, FIG. 33

Chain formation induced by liquid electrodes. Due to particle polarization under pDEP conditions, chains are formed along the electrical field lines. Multicellular structures can be created in this way, and fusion leads to multinuclear cells

FIG. 34 nDEP barrier using liquid electrodes and liquid flow. Under nDEP conditions, the cell is repulsed by the fringing electrical field. Using the balance between viscous drag and nDEP force, the cell can be stably maintained in front of the nDEP barrier. If a second such structure is used simultaneously, the cell can be stably captured between two nDEP barriers.

FIG. 35

Cell electroporation and cell lysis. The electrical field from two liquid electrodes is used to electroporate a cell reversibly, or to lyse it irreversibly if the field is strong enough. In both cases, after a pulse for electroporation or cell lysis, the cell can be monitored via impedance measurement. In the case of electroporation, this gives an indication on the state of the created membrane pores, in case of the cell lysis, intracellular organelles can be analyzed, especially the membrane bound structures such as ER and mitochondria.

FIG. 36

Outline of a fabrication method. Glass wafers (for instance, float glass, 550 µm thick, 100 mm diameter) are used as a starting material. A lift-off photoresist (e.g. TI 35, LOR, Ma-N or others) is deposited by spin coating and then exposed through a chrome mask. A layer of 20 nm of Titan is then deposited by sputtering, followed by a layer of 200 nm Platinum. Lift-off is achieved in remover ( ) combined to ultrasound, leaving the patterned electrodes on the wafer. After a oxygen plasma descum (400 W, 4 min), the negative tone photoresist SU-8 is spun on (20 μm thickness). It is exposed through a chrome mask, and developed in PGMEA followed by isopropanol and distilled water. A second oxygen plasma treatment is performed to free the electrode surfaces from rests of SU-8 (1 min, 50 W). The whole structure is sealed by a flat piece of PDMS with moulded or stamped access holes. Beforehand, the PDMS lid is activated in oxygen plasma (30 sec, 50 W). As the PDMS is not bonded but reversibly sealed, the cleaning procedure consists in taking off the PDMS lid and washing the PDMS lid and the chip with a sponge. Before assembling the chip again, it is advantageous the activate the PDMS lid again in oxygen plasma (again 30 sec, 50 W), in order to favour priming of dead ending parts of the chip. Interfacing with macroscopic fluid reservoirs can be via tubing or by placing a Plexiglas block with integrated reservoirs on top of the PDMS.

FIG. 37

Bipolar measurements of impedance across the main channel for different conductivities. Given are the magnitude of the impedance in ohms on the y-axis, and the frequency on the x-axis (upper graph), as well as the phase in degrees on the y-axis vs the frequency on the x-axis (lower graph). The measurements were taken using an Agilent 4942 impedance analyzer according to the manufacturers instructions.

FIG. 38

Schematic 3D-view of a typical embodiment, where a liquid electrode is in contact with a fluidic channel. For visualization, the covering lid has been partially removed. The LE chamber is defined in photoresist (3803), with a metal electrode patterned on the floor (3801). It opens into the main channel (3804) via an opening (3802).

FIG. 39

Sensitivity of bipolar and tetrapolar measurements. The sensitivities indicated are for coplanar electrode stripes of finite and equal width with a spacing equal to the width, in contact with a half-plane of conducting medium, the sensitivity plots being taken from the center of a given stripe up. In the bipolar configuration, the sensitivity plot is the same above both electrodes. For the tetrapolar configuration, the injection electrodes are assumed to be the outer pair, the pickup electrodes the inner pair, the sensitivity plot being obtained on one of the pickup electrodes. The simulation was by Mathematical. The x-axis is the distance from the electrode surface, the y-axis the sensitivity. The bipolar measurement sensitivity is very high close to the electrode surface, whereas the tetrapolar measurement is more sensitive further away from the electrode surface and thus relatively inert to the electrode surface state.

FIG. 40

Single conduit Dynamic Liquid Electrode (DLE). The shape of a liquid electrode is modulated dynamically by the controlled electrolyte flow through the LE aperture. Its electrical characteristics depend on the geometry, but also on the properties of the fluid in the working zone and of the electrolyte in contact with the LE chamber. Applied voltage and hydraulic pressure are independent.

FIG. 41

A pair of facing single conduit DLEs spanning across a microfluidic channel. The flows through the LE apertures may be used to modulate the shape of the working zone by lateral pinching of a main flow. This sheath flow may act as current insulator or enhancer, depending on the nature of the injected electrolyte.

FIG. 42

Multiple conduit DLE. The electrolyte flowing from a first LE aperture into the main cavity is pulled back through a second LE aperture. Net fluid injection can be prevented by balancing the quantity of injected liquid with the amount of liquid drawn into the second electrode. Depending on the miscibility of the electrolyte with the main buffer, diffusion of chemical components occurs. The shape of the DLE is controlled by the arrangement of the apertures and of the applied pressures.

FIG. 43

Facing multiple conduit DLEs. Dynamic liquid electrodes are arranged in a way to modulate the pinched working zone situated between two multiple conduit DLEs. Such an arrangement is suited for a dynamic optimization of the detection volume for measuring particles in flow. To a certain extent, the detection volume may be adapted to measuring a given particle size without changing microfluidic geometries.

FIG. 44

Variations around a typical embodiment of a liquid electrode. A solid state electrode (4401) is patterned on the bottom (and/or ceiling/sidewalls) in a liquid-filled microchamber (4402). The chamber is connected to a working zone (4403). The connection part between these two areas is an opening (4404) ending a cavity. The corners of the LE aperture can be squared, rounded (4405) or pointed (4408), smooth or rough, concave or convex. The geometry affects the electric field distribution. Moreover, the LE conduit can be supplemented with additional lateral channels in the micro or nano scale (4406) in various configurations and heights. For fast delivery of reagents, the loop shaped configuration (4407) is particularly useful.

FIG. 45

Variations in the diameter of the main channel. Along its trajectory from one electrode pair (V1/V3) to the other (V2/V4), the main channel may vary in diameter, for instance, it may narrow progressively. Applications include longitudinal position sensing and membrane capacitance determination using a single excitation frequency.

FIG. 46

Multiple pickup electrodes for longitudinal tomography applications. Current is injected by a current injector pair (4601, 4602), and potential sensed by 3 or more pickup electrodes (4603-4605). This allows the determination of the impedance in each of the segments delimited by the apertures of the pickups.

DETAILED DESCRIPTION OF THE INVENTION

The Liquid Electrode (LE)
LE 3D Summary [FIG. 1, FIG. 2]
The liquid electrode (0101) is composed of a chamber filled with a liquid (0201) connected to a fluidic cavity (0207), such as a channel, in which the particle(s) or substance(s) of interest are present. The liquid electrode interface (0203) is defined as the equipotential surface spanning across the aperture between its working zone (0208) and the LE chamber.

Liquid Electrode Chamber [FIG. 2, FIG. 38]
The liquid electrode chamber (0201, 3801) can be of arbitrary shape, but preferably it becomes wider with the distance to the working zone. The chamber and the working zone cavity are connected by a short rectangular or differently shaped conduit (0209). The chamber can be covered with a lid of a gas-permeable material such as PDMS (3803). This lid can partially or completely cover the liquid electrode chamber and the working zone. The air trapped inside can then be evacuated by diffusion. The height of the liquid electrode chamber influences the electrical characteristics of the liquid electrode. The chamber can be made much higher than the aperture, to allow for a lower access resistance. A higher chamber also reduces the frequency dispersion (37). The liquid electrode chamber can be equipped with additional fluidic inlets and outlets in the lid or in the side walls, which can be used both initially for facilitating priming, and during operation to apply flow through the liquid electrode chambers (Dynamic Liquid Electrodes, DLE).

Pattern Electrode Patch [FIG. 2]

In the chamber (0201), there is a conductor (0204) which can be connected to the outside world via a conducting lead (0206). The conductor can be made from metal or conducting polymer or any other conducting material that can be deposited. The effective area can be changed by adding nanoscopic structures such as platinum black, or by using microstructured or otherwise formed microscopic roughness on the electrodes. This can be combined with the nanostructuring. Preferably, the conductor is tapered (0205) so that its edge can be brought close to the working zone (0208). Ideally, the conductor has a geometry such that the conductor has a negligible influence on the electric field distribution inside the channel. The electrode may be made up of one or several patches of conductors. The electrodes can be patterned so as to minimize the capacitance between them.

Figure 44:
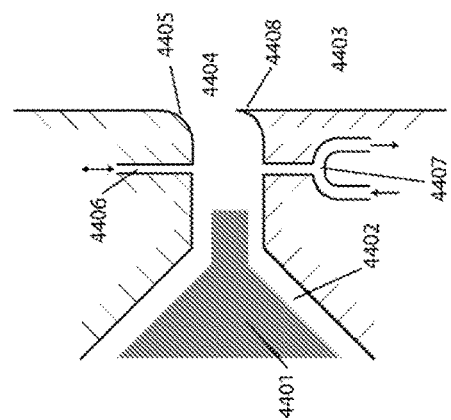

Liquid Electrode Conduit [FIG. 2, FIG. 38, FIG. 44]

The cross-sectional shape of the LE conduit (0209) is influenced by the chosen fabrication technology and can be rectangular (photoresist patterning, vertical dry etching), circular (isotropic wet etching) or determined by crystal planes (anisotropic wet etching). Its layout in the xy plane can be straight or tapered, or a combination of the two. Shorter conduits are characterized by lower access resistance, but higher inhomogeneity of the field in the z-direction.

Aperture [FIG. 2, FIG. 44]

The opening (0203) between the LE conduit (0209) with the patterned solid-state conductor (0204) and the working zone cavity (0207) can intersect the cavity wall at any arbitrary angle. This aperture (0203) can be of the same or a different height than the chamber and the working zone. The LE aperture (0203) can also vary in cross-sectional shape. Generally, it will adopt the cross-sectional shape of the conduit, but it can be controlled independently if needed. For instance, a small circular aperture may be more suitable for certain biological assays than a rectangular one. The corners between the working zone cavity and the conduit (0209) to the liquid electrode chamber can likewise adopt various shapes. Although the usual shape is square, the corner shape may also be rounded or pointed (4405, 4408), smooth or rough, concave or convex. The chosen corner shape influences the detailed field distribution. The electrical field is concentrated by pointed shapes, soft fringing occurs at round shapes. The shape of the corners also affects the fluid flow in the working zone.

Aperture Walls [FIG. 2, FIG. 44]

The aperture walls (or the walls of the working zone) can be equipped with additional lateral channels in the micro or nano scale (4406). They are called lateral nanoslits which are a common denomination for channels with at least one submicron dimension. The geometry can be freely chosen in the xy plane (straight, rounded) and the nanoslits can result of the merging of several inlets (4407). The height can be the same as the liquid electrode chamber or smaller. In case of smaller height, the nanoslits can be fabricated by sacrificial layer (for instance aluminium layer) deposited on the substrate before the polymer coating and dissolved afterwards. A second possibility is using the diffracted light effects in mask openings when exposing the thick polymer. After the development, this can results in V-shaped channels with depth smaller than the polymer thickness. These nanoslits are utilized for injecting one are a mix of several liquids with different electrical properties and can pinch or squeeze the electric field in the aperture of liquid electrode in case of insulating liquids. This also affects the electric field distribution in the working zone. The injection of liquid or liquids through the nanoslits can modify the electrical properties of the aperture by diffusion processes.

Aperture Obstacles [FIG. 6]

The aperture can be equipped with one or more vertical obstacles (0601) spanning the entire aperture height or a portion of it. These objects can span the aperture laterally or horizontally. The apertures allow modifications of the fluid force field (0602) and the electric field (0603) in differentiated ways. An example is that one or several walls, spanning the entire height of the aperture and perpendicular to the flow in the working zone channel (0604), will cause a smaller perturbation in the fluid force field than the same aperture without the protective walls, while having a negligible effect on the electric field. These objects could also be made of a material that allows them to shrink or bend or swell.

Working Zone [FIG. 2]

The working zone cavity (0207) might be filled with the same or a different solution than the liquid electrode chamber (0201). Typically, there are particles suspended on that liquid. The working zone cavity may be a flow-through structure such as a channel or a chamber with in- and outlets, it may also be a zone of no fluid flow. There may or may not be a net flow between the liquid electrode chamber and the working zone cavity.

The Dynamic Liquid Electrode (DLE)

Figure 40:
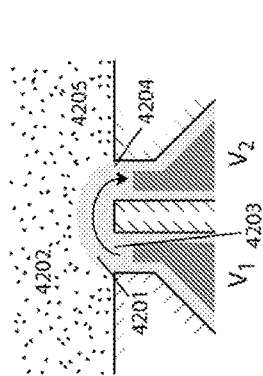

Single Conduit DLE [FIG. 40]

By flowing a preferentially immiscible fluid through the liquid electrode chamber and the conduit, liquid electrodes with dynamically variable shapes can be created.

A simple form of such a dynamic liquid electrode (DLE) is an electrolyte (4001) flowing from a liquid electrode chamber (4002) via a conduit (4003) into the working zone cavity (4004), such as a main channel. Using highly conductive electrolytes, the effective working zone of the DLE can be modulated; using poorly conductive fluids, protective shielding flow patterns can be generated.

Figure 41:
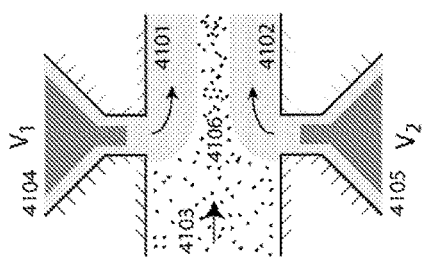

Facing Single Conduit DLEs [FIG. 41]*f*

Single conduit DLEs may be used in pairs, facing across a microfluidic channel. By controlling the pressures applied to the channel in and outlets and to the DLE chambers, the net flow in the main channel can be laterally pinched and the distance between the active surface of the dynamic liquid electrode and the sample can be varied.

Electrolytes (4101, 4102) other than the liquid (4103) present in the main cavity may flow through LE chambers (4104, 4105). If a directed net flow is established, these lateral flows may pinch (4106) the main flow. Depending on the electrical characteristics of the fluid and electrolytes and on the applied pressures, the geometry and the electrical properties of working zone of the dynamic liquid electrodes may be modulated.

Figure 42:
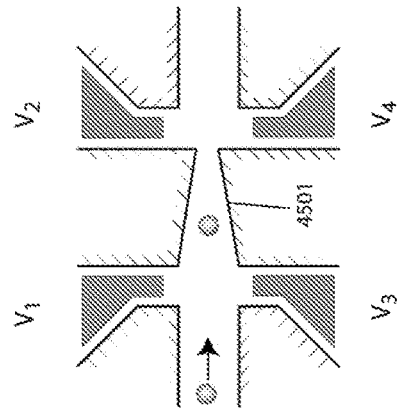

Multiple Conduit DLE [FIG. 42]

In a particular form of the invention, two or more apertures of a LE arrangement may be present in a side-wall of a cavity, and these LE may again be equipped with fluid connections others than the conduits towards the working zones. This permits again to induce net fluid flows into and from the working zones, the fluid injection or retrieval may again be controlled independently of the electric current injection or retrieval. As valid for the single DLE, the injected fluid may be of the same, or of a different composition as the fluid in the working zone, it may contain particles or not.

In a preferred operation mode, the volume of electrode fluid (4201) injected into the measuring cavity (4202) via one or several apertures (4203) is sucked back from the channel via other LE apertures (4204) so as not to interfere with the sample in the main microchannel (4205) further downstream or later in the experiment. For the same reasons, electrode fluids of low miscibility with the sample medium may chosen.

Figure 43:
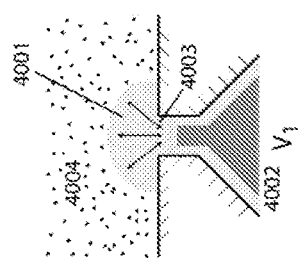

Facing Multiple Conduit DLEs [FIG. 43]

The electrodes can also be arranged into an array of facing conduits. The arrangement of FIG. 43 comprises several electrolytes (4301, 4302) others than the fluid in the main cavity (4303). They are injected through LE apertures (4304, 4305) and optionally reabsorbed through other LE cavities (4306, 4307). The shape of the dynamic liquid electrodes (4308, 4309) depends on the nature of the fluids, the individual pressures and on the individual voltages applied. If net flow in the main working zone of the DLEs is present, the shape of the DLEs may pinch (4310) this flow.

DLE Ensemble [FIG. 19]

Each conduit can be used as a separate liquid electrode with an independent solid-state conductor inside, or the conductor can be made to span both the inlet and the outlet. The protective flow is preferably parallel to the flow in the main channel. The protective flow can also be used for hydrodynamic focussing of particles in the main channel.

Comparison DLE vs. Static LE

In comparison to static liquid electrodes, dynamic LE are capable changing their geometry or chemical composition during operation to some extent. DLEs may be used for e.g. changing flow pattern in the working zone, modulating detection zones impedances, controlling chemical reactions and for bringing auxiliary particles to and from the working zone. Moreover, high conductivity solutions for minimizing access resistance can be employed together with a low conductivity solution in the main flow containing the particles, allowing for low impedance in the liquid electrode paths while minimizing shunting around the particle. For high-resolution impedance measurements, static LE devices may be preferred, as their geometry can be optimised for a restricted range of particles sizes.

Material and Methods

Production [FIG. 36]

An example on how such a device can be manufactured: the electrodes are structured on a glass or other substrate (3601) using photolithography. For example, a lift-off process with a lift-off layer and S-1813 Shipley photoresist (2302) can be used to create a pattern onto which a metal such as Ti/Pt is deposited in thin film, by sputtering or evaporation (3603). The conducting layer can be made up of one or several different metals, for instance titanium or tantal ensure a good adhesion between a noble metal such as platinum and the glass surface. The sacrificial resist layers are then removed using a suitable solvent (3604). The channels and liquid handling structures can then be patterned using a high-aspect ratio photoresist, such as the SU-8 formulation (3605). The SU-8 can be prebaked at 60° for three minutes to improve the adhesion and then exposed to a UV-source for 20 seconds. To remove the modified SU-8 the polymer can be developed in a specific developer solution (3606). To harden the SU-8 it can be cured in an oven with $N_2$ atmosphere.

Preparation [FIG. 36, FIG. 38]

The top part of the channels can be moulded in PDMS, preferably with guiding tracks included in the mould to simplify the alignment with the glass substrate afterwards (3607). To ensure a good seal between the PDMS and the glass surface, a oxygen plasma can be used, typically for 30 seconds. The channels are then filled with medium, which will slowly cover the metal surfaces as the trapped gases evaporate through the PDMS lid.

Signal Detection

Electrical parameters made available by the device may include a potential drop across the measurement volume and the current passing through the same volume. Alternatively, the current is imposed and thus known, and only the voltage drop is measured. These electrical parameters are obtained as full time dependent signal, and are then processed to obtain the desired information. Lock-in detection is an application typically used when periodic signals are applied to the injection electrodes, because it allows for high signal to noise detection for known frequencies. In a more general fashion, any suitable analogue or digital signal processing can be applied to the obtained signals, and may or nay not make use of the information contained in the excitation signal.

Signal Processing

A typical signal processing technique would be Fourier transforms on signals containing information on several frequencies, such as when a frequency sweep pulse is used. Typically, there will be further signal processing such as the analysis of the time course of the signal, including peak detection, amplitude determination, rejection of false positives and specific pattern recognition.

Sample Position Control

The measurements can generally be done in a flow-through manner or by monitoring the changes observed in a stationary sample within the measurement structure, or in a stopped-flow manner, where the flow is stopped when a particle is in the measurement region, and reinitiated after performing the measurement. Flow-through and stopped-flow measurements can be performed with or without prior hydrodynamic, electrical or other focusing of the sample. There may be several measurements performed on a given particle. It may or may not be followed by a sorting mechanism based on the electrical measurements. The sorting step can for example involve DEP, ultrasound, electroosmosis or hydrodynamic control. The control of the position of a sample inside the measurement volume can be achieved by fine flow or pressure control, sedimentation, surface adsorption, cellular recognition of micropatterned and/or chemically modified surfaces, inclusion into a gel or solid formed by chemical or photochemical reaction, blocking of access channels, thermal phase changes, particle trapping methods such as optical, acoustical or dielectrophoretic trapping, and other methods. After an incubation or measurement period, the sample may be released by ending the trapping mechanism, such as by switching off an optical or dielectrophoretic trap, or dissolving a hydrogel. The sample may then be further processed, analyzed or incubated by any device or method that is compatible with the invention. There may be repetition of such measurement and processing phases.

Advantages with Liquid Electrodes

The advantages with the liquid electrodes as described here include but are not limited to a) a broader bandwidth for current injection and pick-up due to a lower solid-state-electrolyte interface impedance due to the larger size of the interface. b) a more homogeneous field at the aperture as compared to the electric field at a solid-state electrode. C) easy cleaning d) longer life-time since lower current densities can be used to produce the same field inside the main channel e) reduced risk for exposing the biological specimen to toxic products created at a solid-state interface f) less drift due to speed variations g) less drift over time h) optimized access resistance to maximize the signal from the specimen. Extra advantages with liquid electrodes using a protective flow over the electrodes include a) protecting the electrodes from fouling agents in the sample b) the possibility of controlling the surface of the liquid electrode by controlling the relative pressures of the liquid in the main channel and the protective flow liquid.

Less pronounced temperature variations. Further advantages include a) particles do not get in direct contact with surfaces others than the channel walls and—as the electrode patches in the liquid electrode chamber are more stable—less electrochemical by-products are released into the working area; in the case of dynamic liquid electrodes, the controlled supply and evacuation of biological/chemical products or thermal energy can render a system even less disturbing for biological cells or tissue cultures.

The liquid electrodes can for example be used for injection of electric currents and measurements of electric voltages.

The Liquid Injector

The liquid current injecting electrode is composed of a liquid electrode and an instrument for imposing a precise direct or alternating voltage or injecting a precisely controlled current. The aperture for the liquid injector can be made rounded to reduce the local heating at strong fields.

The injection electrodes are driven using a DC or AC signal, which can be composed of single or multiple frequencies or follow an arbitrarily defined waveform or pulse, such as a step, triangle or frequency sweep (chirp). Generally, but not necessarily, an electrical parameter such as current in the case of a voltage-controlled signal or voltage in the case of a current-controlled signal will be monitored for the injection electrodes.

The Liquid Pick-Up

The liquid electrode pick-up electrode is composed of a liquid electrode connected to a voltage or current measuring circuit. The liquid pick-up electrode is particularly useful in tetrapolar measurement arrangements and arrangements including an ensemble of injection sites and measuring sites such as resistivity imaging devices.

The advantages of the liquid electrode pick-up include the possibility of performing measurements at low frequencies (down to 50 Hz or lower). Moreover, as opposed to a conductor placed at the same position in the main channel, the liquid pick-up electrode will not distort the electric field as much. This is because the metal is a good conductor, making it an effective equipotential surface, which is not the case with a liquid aperture. A solid-state pick-up electrode also has an interfacial capacitance, which means that the induced distortion will depend on the frequency, which is not the case for liquid electrodes.

Figure 8:
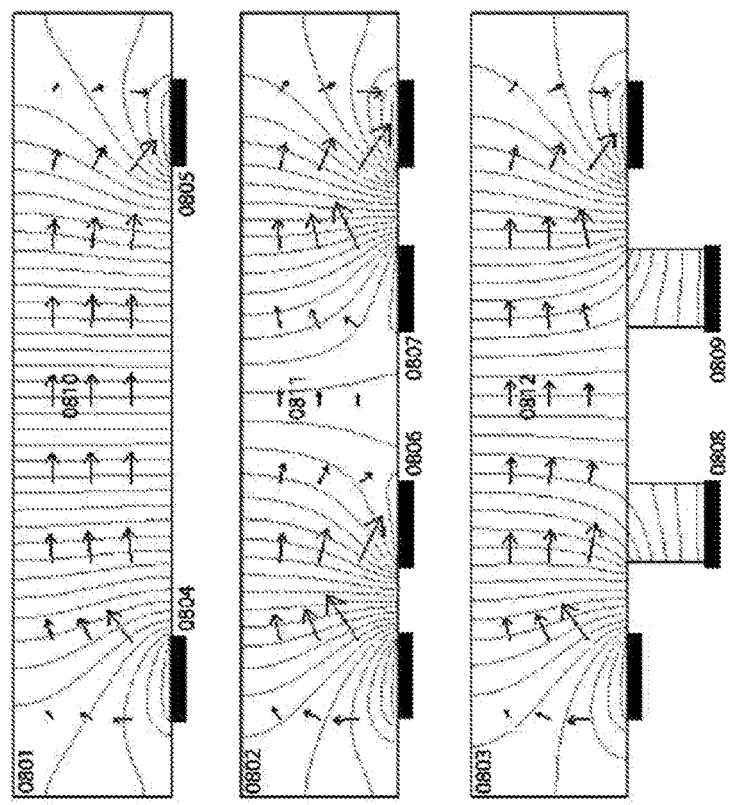
FIG. 8
Disturbance of the electrical field by classical microelectrodes as compared to liquid electrodes as simulated by the finite element method (FEMLAB) in a coplanar geometry. The field imposed by a pair of classical microelectrodes in a microchannel is quite homogeneous in its central part (0801), but adding supplementary measurement electrodes leads to inhomogeneity because of the coupling of the current in and out of the electrodes (0802). Using liquid electrodes, this effect is dramatically reduced (0803)

Example of Field Distortion [FIG. 8, FIG. 9]

To demonstrate the advantage with the liquid electrode pick-up we have performed a number of finite element simulations using the software package FEMLAB. As an example of field distortion using conductors in the main channel FIG. 8 represents an electric field simulation (0810) of a tetrapolar arrangement (0802) using conductors (0806, 0807) placed in a channel, and subfigure (0803) represents the field lines (0812) in the channel using liquid electrodes (0808, 0809) for the voltage pick-up measurements. A different situation is shown in FIG. 9.

Pick-Up Electronics

The liquid pick-up can be made of any aperture size and can for instance be made smaller than the main channel so as to probe the potential in a small segment only. The liquid pick-up electrode can for instance be connected to an instrumentation amplifier or directly to a lock-in amplifier such as the Stanford Research Systems SR844RF. The pickup electrodes are used to measure the potential at their location in the main channel, which requires electronics consuming as little current as possible. Typically, voltage buffering with low bias current operational amplifiers will be employed, and techniques such as bootstrapping and or capacitance compensation will be taken to minimize the effect of parasitic capacitance in the AC domain.

The determination of the potentials at the pickup electrodes, or the difference between the potentials at the pickup electrodes, can be done using for example a bridge-measurement or a lock-in amplifier. The lock-in measurement can measure at the same or a different frequency as that injected through the injection electrodes, an in-phase and out-of-phase components of the signal. By measuring either generation of superior harmonics or direct observation of the response to different stimulation amplitudes, non-linear electrical behaviour can be detected and analyzed.

Guard Electrodes

Supplementary electrodes, which may be composed of stripes of metal or liquid electrodes or conducting organic material or any combination hereof, and may or may not be in electric contact with the liquid, can be driven at potentials equal to or different from the injection and pickup electrodes, can be used as guard electrodes. Guard electrodes may serve both to restrict the measurement volume by guiding the relevant fields and as a measure against parasitic capacitance and noise pickup.

Tuneable VHF Elements

By properly engineering the liquid electrode chambers these can be used as resonance cavities for VHF elements. The liquid electrode can then be used as an emitter, with an emission peak in the radio or microwave band.

Design Rules

The pick-up electrodes should preferably be placed a certain distance into the conduit, and this distance should preferably be equal to or greater than the conduit width in order to obtain a homogeneous field at the liquid electrode surface. The distance between the electrode patch and the main channel should be small to reduce the access resistance. The injecting electrodes should be far from pickup electrodes to avoid capacitive pickup at higher frequencies, for instance, injection electrodes can be located on one side of the main channel, while pickup are located on the other. Triangular shapes are of considerable use, as they limit the impedance of the liquid electrode effectively at both high and low frequencies.

The Liquid Electrodes Assembly

The liquid electrode can be combined into several structures having unique properties, where the principal advantages are an increased frequency range, a longer life time, reduced heating and contamination and a negligible frequency-dependent field distortion.

Liquid electrodes can also be used in conjunction with other techniques as will be evident to the person skilled in the art. LE might be used with passive or active field constrictors, liquid flow injection, deviation, filtering and suction.

Impedance Measurements

Regular Bipolar

Liquid electrodes can be used to perform impedance spectroscopy of particles in a flow-through manner, or of stationary particles or other kinds of samples in a channel. Preferably, the liquid electrodes are placed at right angles to the main channel.

Differential Bipolar [FIG. 4, FIG. 18]

Typical examples of adaptation of established solid-state electrodes applications to LEs applications are bipolar impedance measurements between facing electrodes both in direct and differential (4) configurations, without or with (18) guarding (confinement of the electric field in the detection zone by electric fields between auxiliary electrodes). The liquid electrode concept can also be applied to the tripolar measurement method.

Asymmetric Coulter Counter [FIG. 21]

Liquid electrodes can inject/pickup electric signals at large bandwidth, a pair of LE designed for making bipolar impedance measurements does not necessary have to be facing in either the perpendicular of parallel direction to the particle flow. In particular, a pair of LE for impedance measurements can be placed laterally to a fluidic channel, up- and downstream of a single or a series of orifices through which particles can flow. The lateral asymmetry of the sensing field will produce an asymmetric response (2101) depending on the particles lateral particle position and on orifice(s) size and location. Such a configuration can be considered as a mixture of a longitudinal bipolar Coulter counter and a transverse—position sensitive—impedance sensor.

Asymmetric Lateral Position Detector [FIG. 21, FIG. 21]

An asymmetric positioning of LE up- and downstream (2104, 2105) of multiple flow constrictions (2102) allows for particle dielectric characterization combined with speed detection and positional sensing.

Constrictions concentrate the electrical field and give rise to stronger signals for a given particle or liquid volume passing through the structure at a given place. This can be used to generate a position dependent signal. For example, if the particles in FIG. 20 or 21 pass along a line y>0, the first peak in the signal vs time diagram will be smaller than the second peak, generated as the particles pass through the concentrated peak at the aperture between the rightmost constrictions. A combination of two constrictions (2102) can be used to determine particle or plug flow speed, since the time course of the signal depends on the speed of particle or plug.

Figure 45:
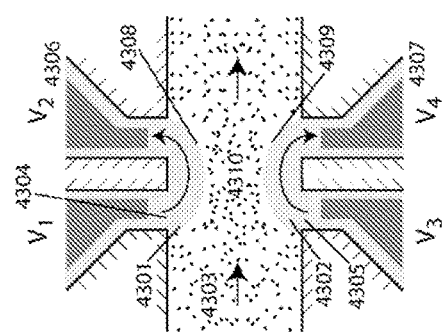

Progressively Narrowing Longitudinal Position Detector [FIG. 45]

A progressive narrowing (4501) gives an increasing signal when a particle moves to the narrower part. This can be used as an electrical position sensor for a given particle or plug. In combination with an arrangement where the injection electrodes are on opposite sides of the channel (FIG. 21), lateral position sensitivity can also be achieved. Lateral and longitudinal position sensitivity in flow through devices can then help improve cell sorting.

Geometrical Impedance Spectroscopy [FIG. 45]

The proportion of current flowing through a particle and around it depends on the relative impedance of the environment and the particle. Thus, the impedance spectrum of a particle will not only depend on the properties of the particle, but also on the geometry of the channel and the electrical properties of the medium. Impedance spectra at different channel widths give thus rise to supplementary information concerning particle and environment impedance. The variation in channel diameter in the main channel may be progressive (4501), but discrete steps are also possible. In a flow-through apparatus with width variations of the central channel, this allows for more exhaustive analysis of impedance parameters of the particle, such as cell membrane capacitance and cytoplasm resistivity and permittivity for cells, and dielectric and resistive properties of particles in general, even if only a single excitation frequency is used.

Temperature Considerations

When working with living biological matter, exceeding physiological temperatures may result in irreparable damage. Electric current passing through a conducting medium results in Joule heating. Several methods of in-situ temperature measurements are available, many of them yield results averaged over the channel height when temperature patterns near electrodes on top and/or bottom are to be characterized. Additionally, in the case of opaque electrodes in planes perpendicular to the direction of observation, optical masking occurs for both illumination and observation. Using liquid electrodes more precise temperature distribution maps can be acquired because no part of the working zone is optically hidden by the metal patches. Various techniques of temperature determination can be used, such as fluorescence quenching or thermal precipitation of suitable polymers.

The use of LEs instead of metal electrodes can for example lower the risk of having zones of damaging temperatures, appearing where the current densities are very high. With metal electrodes, current densities are unavoidably highest at electrode edges and tips; with liquid electrodes, the homogeneity of electric filed distributions can be engineered, and therefore, a much smoother current distribution can be obtained (soft fringing).

Tetrapolar Measurements

Summary

An embodiment of the invention for impedance measurements consists of four lateral electrodes in contact with a channel or capillary (FIG. 5). For an extended bandwidth, especially towards lower frequencies, the electrodes should be liquid electrodes, but for higher frequencies metal or polymer electrodes patterned onto the side walls of the channel are also possible. In the preferred embodiment with liquid electrodes, the metal patches are located on the floor of the liquid electrode chambers, as shown in FIG. 38. In addition, the walls of the chamber could also be metallized, although this is technically more difficult. A mirror image of the metal patch on the floor could be patterned onto the lid to further increase the active surface, but then precise alignment between the lid and the chip is required.

Variations include supplementary electrodes for supplementary functions (such as FIG. 18), the use of dynamic liquid electrodes (FIG. 43), the use of guard electrodes (FIG. 18), the use of constrictions in the main channel (FIGS. 17 and 20), a tapered main channel (FIG. 45) and application of some focusing mechanism such as DEP or hydrodynamic focusing to reduce variations due to later positioning, and the use of branched liquid electrode structures (FIG. 3).

In this particular embodiment of the invention two (or more in case of guard electrodes) electrodes are used to change the electrical state of the system, generally by injecting a current or imposing a voltage. These quantities may or may not change with time. Two or more pick-up electrodes are used to measure the electrical potential or the potential difference between two points of the microstructure. The electrodes can be placed on either side of the channel, typical configurations being two injection electrodes on one side of the channel, each of which faces a pickup electrode (FIG. 5). An alternative configuration would consist of four electrodes on the same side of the channel, two of them used as injection electrodes, the other two being pickup electrodes, but other arrangements are also possible.

Advantages with this Measurement Device

The advantage with this arrangement is that the measurement volume is smaller than in microsystem measurement setups where all electrodes are placed in the same plane. Compared to bipolar measurements, tetrapolar measurements eliminate to a large extent the influence of the electrode surface state; however in a coplanar arrangement due to capacitive coupling in and out of the electrodes that lie in the current path, an uncontrolled element is still present in measurements. Using electrodes on the walls at suitable positions helps limiting this effect.

When liquid electrodes are used as pickups, this advantage is particularly pronounced, as they show very little perturbation of the field to be measured. They shunt very little current through the metal by capacitive coupling into the electrode and out again on the other side (FIG. 8), because the metal electrode is generally outside the main current path as imposed by the injection electrodes. This enables precise measurements over a wide range of frequencies and pulse shapes with minimal influence of the electrode surface states.

In the particular configuration where a pair of injection electrodes on one side of the channel and two pickup electrodes each facing an injection electrode are used, there is a compensation effect between the field intensity and the pickup sensitivity. The injection field is inhomogeneous, being stronger close to the channel side where the injection electrodes are located, but the pickup is more sensitive to field changes close to the opposite channel wall, giving an overall sensitivity profile across the main channel that can be homogenous to within less than 5%.

As compared to a Coulter counter setup using a membrane, the invention adds the possibilities of microfluidic control due to the possibility to integrate a sophisticated channel network.

Applications of the Measurement Device

The invention can generally be used to precisely measure the absolute magnitude as well as changes in electrical parameters of the small sample volume in the measurement channel. Primary electrical parameters typically obtained are voltage drop and current through the measurement volume, allowing for the calculation of the measurement volume complex impedance. The information can be further used to deduce secondary parameters influencing the electrical properties or their evolution with time, such as specific material properties such as permittivity and resistivity, temperature, diffusion properties and flow speed, chemical reactions and states such as pH, biochemical reactions such as DNA hybridization or protein binding, cellular proliferation, migration and differentiation, presence of particular biological species such as biological molecules, bacteria, viruses or cancer cells as well as parasites contained inside cells, electrophysiological phenomena such as changes in membrane permeability or action potentials of excitable or spontaneously active cells or cell groups, morphological changes of biological or chemical species such as muscle cells or environment-responsive hydrogels, composition and contamination of food related products, reactions to pharmaceutical agents by cells as evidenced by change in electrical parameters, and many more. The nature of the sample can be a homogenous liquid, gel, solid or gas, a suspension of particles, cells for instance, or an emulsion of two or several phases, including an ordered droplet or bubble stream. The origin of the electrical characteristic to be measured may be manifold, including but not limited to changes in the liquid, the particles, especially cells and their membranes as a reaction to various conditions and agents, surface reactions on beads or other carriers, bulk reactions such as precipitation, heat generation, production or consumption of conductive chemical species, the passage of a particle in relation to the geometry of the measuring device, active transport of charges by living organism, diffusion and streaming potentials, substance accumulation or depletion. When measuring single or few particles, care will generally be taken to fabricate the measurement channel on the same size scale as the object to be measured, in order to improve signal to noise ratios. According to the arrangement of the electrodes, spatial inhomogeneities in electrical or related parameters, as well as anisotropic parameters and non-linear responses of tissues and cells can also be measured.

Impedance Tomography

Summary

The basic principle of a tetrapolar measurement with microelectrodes, such as liquid electrodes, contacting a central measurement cavity can be extended and varied. Extending the number of electrodes allows for tomographic applications. This can be achieved by using a fixed pair of injection electrodes and an arbitrary number of measurement electrodes contacting a measurement volume at different points (e.g. FIG. 29). In a more sophisticated manner, there may be dynamic re-routing of the electrodes to the signal injection and measurement apparatus. In both ways, information ranging from a simple overall estimation of impedance anisotropy to tomography of the measured particle can be achieved, depending on the number of electrodes implied and the reconstruction algorithm employed.

Figure 46:
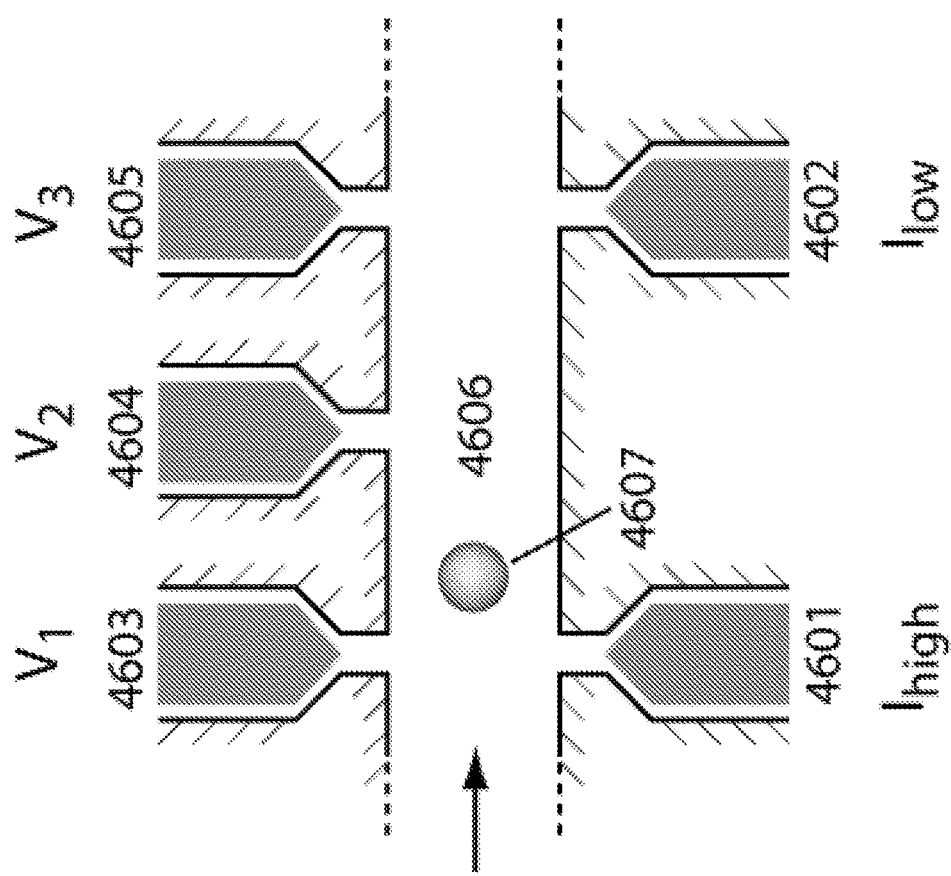

Several Pick-Ups in the Channel [FIG. 46]

Another variation related to tomography is multiple pickup electrodes along the main channel, as shown in FIG. 46. In its simplest embodiment, voltage is also measured in the middle of measurement channel (4606), giving rise to a total of three pickup electrodes (4603-05) associated with two injection electrodes (4601, 4602). This allows detection whether a particle (4607) is in the first or second part of the measurement channel, alternatively the impedance measured in the first and second part can be subtracted in order to obtain a differential measurement. Differential measurements are less sensitive to global conductivity changes in the measurement channel. The subtraction is preferentially achieved by subtracting the corresponding buffered voltage signals, as the current is common to both parts of the measurement channel, but direct numerical subtraction of impedance values is also possible. In order to limit parasitic capacitance effects, counter-phase current injection may be used. More precise position localization can also be achieved by a series of pickup electrodes localized along the main channel, still using one pair of injection electrodes supplying the current of the whole structure.

Lateral Electrodes for Electrokinetic Particle Manipulation

Summary

The use of lateral electrodes instead of opaque electrodes patterned on the top and/or the bottom of a transparent fluidic cavity yields the advantage of the unobstructed view of the working zone of the electrodes, in addition to the potentially larger coupling surface minimizing the current densities when using liquid electrodes. Electrokinetic phenomena accessible with lateral and/or liquid electrodes include electrorotation, electropermeabilization, electrodeformation, electro fusion, electrophoresis and electroosmosis, as well as nDEP and pDEP with their manifold applications ranging from trapping and perfusing to dipping and sorting.

Figure 25:
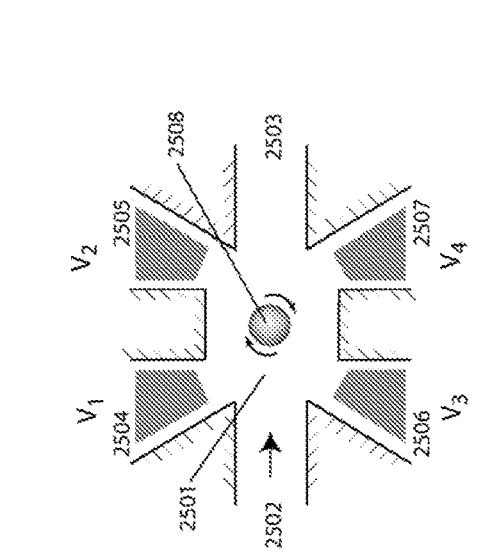

Electrorotation, 4-Electrodes Structure [FIG. 25]

Electrorotation is carried out in homogeneous, rotating electric fields between typically four electrodes. The better the homogeneity, the less parasitic dielectrophoretic effects occur. Lateral electrodes yield fields that are homogeneous in the z direction, the distribution of their field in the x and y directions is given by the geometry of their arrangement. FIG. 25 depicts a chamber (2501) having an inlet (2502) and an outlet (2503) channel. Four lateral electrodes (2504-07) are arranged at the chamber sidewalls and one or several particles (2508) can rotate at the center of the 4-electrodes structure.

Figure 27:
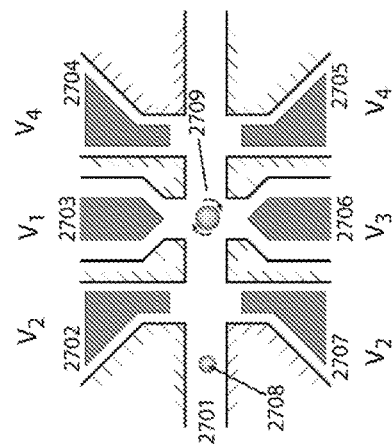

Electrorotation, 6-Electrodes Structure [FIG. 27]

Other than 4-electrodes electrorotation structures with enlarged central chambers, 6-electrodes structures (typically using a four phase current injection scheme) can be used for electrorotation in very confined volumes still featuring highly homogeneous field distributions. The enhanced field homogeneity is obtainable by the combined arrangement of lateral electrodes and fluidic channels. A 6-electrodes structure is shown in FIG. 27. A fluidic channel (2701) is intercepted by 6 lateral electrodes (2702-07). For particles (2708) flowing from left to right, the combination of the four first electrodes may be used for a dielectrophoretic centering (nDEP valley) before entering the rotation zone (2709).

Electropermeabilization Perpendicular [FIG. 35]

Lateral electrodes may be used to inject fields perpendicular to the channel axis. Particles on the working zone are subjected to static or pulsed electric fields of strengths typically above 1 kV/cm. The shape of the field may be engineered by the geometry of the system. Homogenous field may be preferred, for the lack of dielectrophoretic components and for the more accurate modelling of the influence of the field on the particle. Facing pairs of wider lateral electrodes result in more homogeneous fields.

Particles may be stationary in the working zone, they may be flowing through, or a timed sequence of the two modes. For cells, vesicles or similar biological objects, the electric fields may be used to induce a membrane breakdown, the membrane may be permeabilized reversibly or irreversibly (lysis). The cell carrier medium may contain substances that may diffuse into the cell during the permeable state of the membrane, the presence of genetic material may result in transfection. Extraction of intracellular content (cell lysis) and cell death may be achieved by the application of excessively high field strengths and/or by Joule heat treatment at the same location. Lateral electrodes for perpendicular electropermeabilization may be implemented as liquid electrodes.

FIG. 35 shows a possible electropermeabilization or heat treatment configuration. Between two facing lateral electrodes (3501, 3502) a homogeneous field zone (3503) is created across a fluidic cavity such as a channel (3504). A particle (3505) or several particles reside at or flow through this zone.

Figure 26:
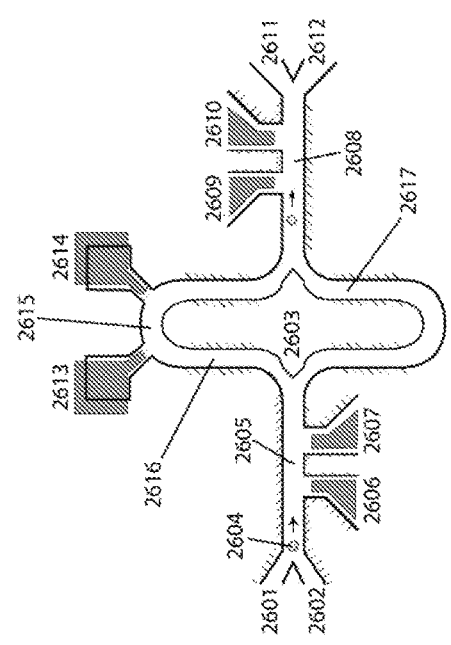

Electropermeabilization parallel [FIG. 26, others like FIG. 21]

Lateral electrode configurations for electropermeabilization or heat treatment are fields parallel to cavity walls and flow directions are e.g. depicted in FIG. 26 or schematically in FIG. 21.

An electric field (2615) may be created in curved channel systems (2603) between two lateral electrodes (2613, 2615), or across one or several channel restrictions (2102) between lateral electrodes (2104, 2105). In any configuration, buried lateral electrodes or liquid electrodes may be used.

pDEP Structures for Electrodeformation [FIG. 28]

For the abovementioned reasons of visibility, electrodeformation of cells can be particularly well observed when lateral electrodes are used. Electrodeformation occurs under pDEP conditions, at frequencies that are medium and particle properties dependent. Using planar electrodes the electric field is inhomogeneous in the xy plane, but also in the z direction. Lateral electrode configurations offer more homogeneous fields in the z direction which facilitates modelling. From the amount and time constant of deformation and relaxation, important cell-relevant information can be retrieved. The electric distribution can be engineered by the applied voltages and the width and arrangement of the lateral electrodes, thinner electrodes resulting in more pronounced field fringing. If liquid electrodes are used, the width of the electrode aperture must be engineered smaller than the particle size. A possible electrodeformation configuration is shown in FIG. 28. One or a multitude of particles (2801) is guided by a channel system (2802) to the working zones (2803) of one or several pairs of lateral electrodes (2806-$n$). Particles are attracted by fringing fields (2804) towards the lateral electrodes. If biological cells are used, they may enter a deformed state (2805).

pDEP Structures for Electrofusion [FIG. 32, FIG. 33]

The attraction of particles by positive dielectrophoresis towards high field strengths at thin electrodes in large or open fluidic cavities may result in pearl-chains of particles. Pearl chains are created because the highest electric field gradient always occurs at last particle which acts to some extent as an electrode tip. New particles are attracted towards these tips and they become the new tips which makes the chain grow. Pearl chain formation using lateral electrodes is shown in FIG. 32. The voltage applied to a fine lateral electrode (3201) with its working zone (3202) oriented towards a counter electrode (3203) has attracted several particles (3204). Another particle (3205) is being attracted towards the tip of the existing chain. Once a pearl chain of two or more biological cells is established, one or a series of strong electric pulses can be applied by superimposition to the pDEP signal. Under the right conditions, the cell membranes at the facing poles can be disturbed in a way that cell fusion occurs. pDEP-mediated electrofusion allows for the artificial creation of hybrid cells.

Cell fusion using lateral electrodes is shown schematically in FIG. 33. The membranes of cells of a previously formed chain (3301) are rearranged and their content is direct contact.

Electrophoresis and Electroosmosis

Other DC and AC electrokinetic effects such as electrophoresis can also be studied using lateral electrodes. These electrodes may again be solid electrodes made of conducting materials placed at the sidewalls of microfluidic chambers, or they might be liquid electrodes.

Lateral DEP Structures

Summary

A very efficient manner of handling particles in microchannels is the use of lateral negative dielectrophoresis (nDEP). Arrangements of lateral electrodes can be used to repulse and thus to sort suspended particles laterally in flow, to focus them onto one streamline or to push them into auxiliary channel outlets. The term lateral means that the electrodes are perpendicular to the substrate and parallel to the light-path of the microscope used to observe the structures. Our invention makes use of one or more lateral electrode in a microcavity combined with other electrodes (additional lateral electrodes, metal electrodes inside or aside the channel). The electrodes might be liquid electrodes as described above, or solid state electrodes as known in the art, or a combination of the two.

Our invention is able to generate a dielectrophoretic potential inside a channel. All the configurations combining at least one lateral electrode with any other electrode for manipulating particles with dielectrophoresis (DEP) are stated as lateral DEP structures. Our invention can generate positive or negative dielectrophoresis relatively to the permittivity and conductivity of the medium and particles. However, essentially the negative DEP (nDEP) is considered in the applications exposed in the next sections. nDEP generated from lateral electrodes is comparable to classical nDEP generated from top and down metal electrodes as exposed in the background section. However, the great advantage of lateral DEP structures is the fact that the force act in a direction parallel to the substrate instead of acting along the height axis. This fundamental difference makes the sorting of particles much easier since the force can deviate them along a direction parallel to the bottom of the channel.

Moreover, the design of the main channel and lateral electrodes can enhance inhomogeneities of the electric field in some places while making it uniform in other regions. This characteristic results in an in homogenous distribution of the force along the channel which is controllable by the geometry and the arrangement of lateral electrodes along this one. Especially the access channel, between the lateral electrode chamber with the electrical pad and the main channel, is a geometrical factor that can be exploited for generating interesting singularities in electric field distribution. Its length, its direction and its shape of the crossover with the main channel can act as local trap or in the opposite as repulsive area. Simulations of the distribution of the electric field inside the structure and the modulation of this one by geometrical factors are presented later in the patent.

nDEP Structures for Sorting [FIG. 10, FIG. 11]

This section aims to describe the variety of applications where the DEP is generated by the combination of at least one lateral electrode with at least one other electrode along a main channel. The FIG. 10 presents an example of lateral DEP structure formed by two lateral electrodes located in the same side of the main channel. The dielectrophoretic force is generated when the inhomogeneous electric field is created between the two electrodes. It is assumed that the electrical properties (permittivity and conductivity) of the medium and the particles in suspension impose nDEP. Thus, the configuration in FIG. 10 leads to nDEP that tends to deflect the dielectric particles towards the opposite side of the main channel. The lateral electrodes have the capability of deviating flowing dielectric particles along an axis parallel to the plane of observation. If the main channel separates in several channels afterwards, the perpendicular force can select the output that each particle will take by controllable deviation. Many geometrical factors are customizable like the distance between the two electrodes, the shape of the corner between the main channel and the access channel of lateral electrodes (1001), the width of the main channel and the distance before the main channel splits in several outputs. Alternatively, an additional output channel can be disposed along the side facing the lateral electrodes. The FIG. 11 shows an example of design. In this case, the perpendicular nDEP deflects the particles into this additional output channel. The geometrical aspects like the width, the exact position and the direction are flexible. Several identical structures can be placed behind each other and provide a multi output sorter.

Alternative nDEP Structures for Sorting [FIG. 12, FIG. 13]

Two lateral electrodes can also be placed facing each other. The FIG. 12 presents one possibility. The openings of the two facing lateral electrodes differ in size. The section of the upper electrode (1201) is wider than the lower electrode section (1202). This difference serves as creating an asymmetric inhomogeneous electric field. The resulting nDEP repulses the dielectric particles from the small section towards the wider section and thus acts along an axis perpendicular to the main channel direction. Similarly to the previous configuration, the selection of the output can be tuned by the control of the nDEP magnitude. Additional bars (1301) can be placed in the wider opening for avoiding the liquid of the main channel to enter the lateral electrode. The bars shown in FIG. 13 reduce the flow perturbation without modifying the inhomogeneous electric field distribution. Several pairs of facing lateral electrodes can be placed next each other for obtaining more complex functions like multi sequential deviations. The ratio between the sections of the two facing lateral electrodes determines the electric field distribution. For example, two identical and facing sections would create an inhomogeneous electric field which would be symmetric. The symmetry axis is the half width of the main channel and would consist in the region of smallest gradient of electric field intensity. In this case, the nDEP tends to center and align the particles along the half width axis. All variations in design are possible and customizable for specific applications.

Combo Structures [FIG. 14, FIG. 15]

The use of lateral electrodes can also be combined with traditional, planar metal electrodes. Such combo structures might be useful in certain cases of 2½ dimensional particle handling (levitation), local field concentration, power consumption issues, contact-induced reactions, fabrication simplicity or integration density.

By combining lateral and planar electrodes, an electrical force perpendicular to the main channel can be created. The nDEP acts along one direction and deflects particles towards the side of the main channel which is facing the lateral electrode. The main channel can also contain additional output channel for evacuating deviated particles. A configuration with one lateral electrode, a second metal electrode inside the main channel (1402) and one additional output channel (1401) is represented in FIG. 14. The DEP structure can also consist in two facing lateral electrodes and one metal electrode in the main channel. This configuration based on three electrodes is shown in FIG. 15. If a difference in potential is applied between the metal electrode and one lateral electrode, the resulting force tends to deflect the particles towards the opposite side of the lateral electrode in use. The symmetric behaviour is observed if the potential difference is applied between the metal electrode and the second lateral electrode. Moreover, this configuration allows creating a force that aligns the flowing particles by utilizing the three electrodes simultaneously. For this purpose, different potentials $V_1$ $V_2$ and $V_3$ are applied to the different electrodes. Two electric fields are creating inside the DEP structure. The axis of the particle alignment depends on the ratio between the two electric field intensity. The control of the potentials permits aligning the particles along a tuneable axis and so to select the output.

nDEP Valley [FIG. 16]

The combination of two lateral DEP structures facing each other results in a distribution of the dielectrophoretic force that can align the particles. The two inhomogeneous electric fields interact and create a valley in the force intensity distribution. FIG. 30 shows the results of a finite element simulation on which is plotted the gradient of the electric field intensity. Assuming that negative DEP repulses dielectric particles from high intensity areas, it is obvious that particles are flowing along the low intensity regions that exhibit the shape of a valley (3001). The location of the valley along the width of the main channel is controllable by the ratio between the two inhomogeneous electric fields. An example of such a configuration based on four lateral electrodes is shown in FIG. 16. The dielectric particles in suspension are flowing from the left side to the right side of the figure. The DEP structure has the potential to align all the particles and positioning them accurately and in a controllable manner on the width axis.

nDEP Turn Structure [FIG. 23, FIG. 31]

Different numbers of lateral electrodes, different numbers of lateral channels and the flexibility in geometrical dimensions allow imagining all kinds of nDEP structures for sorting dielectric particles. Even the geometry of the main channel isn't imposed. For example, the main channel in FIG. 23 has a rounded shape. This kind of configuration is called DEP turn structure. A pair of lateral electrodes placed at the extremities of the turn creates an electric field along the turn. Several lateral output channels are disposed along the turn and create inhomogeneities in the electric field distribution. The effect of the geometry on the electric field is represented by the result of the finite element simulation in FIG. 31. The inhomogeneities due to the geometry create regions of low gradient of electric field intensity (3101) that enter the lateral output channels (3102). The nDEP deflects the flowing particles into these lateral output channels. Consequently, the selection of the output channel for each particle is controllable by the timing of switching ON and OFF the electric field. The DEP turn structure presented in FIG. 23 contains five lateral output channels. However, it is customizable and can contain from one to several lateral output channels. This geometry presents the advantage of selecting one among several outputs by the control of only one pair of lateral electrodes.

nDEP Structures for Trapping and Dipping

Liquid electrodes in lateral DEP configurations can be used for the implementation of dielectrophoretic particle handling schemes such as field barriers, particle traps and cages as well as for particle deviation from one carrier medium into another (cell dipping).

nDEP Walls [FIG. 34]

Dielectrophoretic elements such as nDEP walls or barriers rely on the field fringing between two narrow, opposite current injection strips. The corresponding electrode pair might be placed vertically or laterally. In FIG. 34, lateral DEP structures are created with Liquid Electrodes (3401, 3402). The fringing field (3403) repels a particle (3404) flowing in a channel (3405) from left to right. The nDEP wall is effective as long as the dielectrophoretic repulsion is superior to the Stokes drag. The amount of field fringing can be controlled be the sizes and the distances of the LE apertures.

Figure 22:
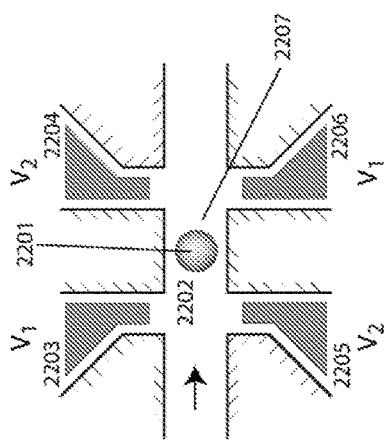

Quadrupolar Field Cages [FIG. 22]

Under nDEP conditions, particles are repelled from high intensity field zones. They can be trapped at the field minima of quadrupolar fieldcages. Field cages may be implemented using four lateral electrodes. One possible method for creating lateral electrodes are Liquid Electrodes. FIG. 22 shows a basic field cage configuration: a particle (2201) present in the working zone (2202) of four electrodes (2203-06) is captured at the field minimum (2207). The location and strength of this field minimum depend on the geometry of the lateral electrode structure and on the applied voltages.

Figure 24:
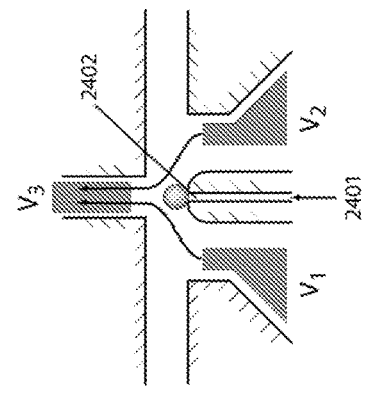

Perfusion Trap [FIG. 24]

The interaction between engineered geometry and electric field generated by lateral electrodes can also create locations where particles are trapped instead of being repulsed. In simulation, such a region of small gradient of electric field intensity is surrounded by a region of high gradient. The particles are trapped by switching ON the electric field and released by switching OFF. The FIG. 24 presents an example of DEP structure with one trapping site (2402). Two lateral electrodes in one side of the main channel and a third lateral electrode in the opposite side create a nDEP distribution provoking trapping sites for dielectric particles. The trapping locations can be accurately defined by engineered geometries and predicted by simulations. Furthermore, the locations can be specially designed for different applications and contain for instance perfusion channels (2401). The repetition of several identical nDEP structures enables a parallel trapping process.

Dipping [FIG. 26]

The combination of a main channel with multi inputs/outputs and the nDEP inside the main channel enables many applications based on the interactions between dielectric particles in suspension in different liquids. Indeed, one or more liquids can be introduced in the main channel by the one or more inputs. The liquids flow next each other without mixing except by diffusion process due to the laminar flow occurring at microscale. A pair of lateral electrodes in one side of the main channel generates a perpendicular force in order to deflect all the particles in suspension in the first liquid (buffer) towards the opposite side of the channel into an adjacent liquid (reagent). Sequentially, a second pair of lateral electrodes disposed along the opposite side of the first pair can symmetrically bring back the particles in the original buffer. By varying flow speeds and channel geometries, the exposure time can be tuned and adapted for specific reactions. These structures allow the user to swap a large number of cells between two liquid environments in a fast and controlled manner. The FIG. 26 presents a nDEP structure specially designed for particle dipping. It consists in at least two pairs of lateral electrodes for A) exposing particles to the reagent (from 2601) and B) bringing particles back into the original buffer (from 2602). The intermediate channel section (2603) can have various geometries for shorter or longer exposure time. It also can separate in two or more channels (2616, 2617) for limiting mixing by diffusion process.

More complex dipping function can also been obtained by using an array of liquid electrodes with different electric signals at multiple frequencies.

Sophisticated Functions

All the applications presented above can be combined for more evolved functions. Several pairs of lateral electrodes can be arranged along the main channel for moving, trapping, sorting and dipping dielectric particles in suspension. For example, particles could be moved from a point to another only by the influence travelling-wave dielectrophoresis. This phenomenon is achievable with DEP structures were several pairs of lateral electrodes are arranged along the main channel and switched ON and OFF sequentially.

The sorting application or separation can be better achieved by applying potentials composed of multiple frequencies. For instance, one can use a DEP valley structure and apply two different frequencies in order to obtain different position of focusing for particles with different dielectric properties. The sub-populations can afterwards be routed to different outlets for separation. The principle can be extended to any combination of potentials and frequencies and in fact arbitrary signals on both sides. The separation efficiency can be increased by using an array of electrodes. The separation procedure can be iterated on sub-populations either on the same chip or by pipetting the sub-population back to the inlet or to another chip.

The invention claimed is:

1. An impedance measurement device for measuring an impedance of flowing particles by an electric field, comprising:
   a channel for conducting a liquid with the flowing particles;
   a first electrode chamber, and a first solid state electrode located inside the first electrode chamber such that a first cavity is formed between the first solid state electrode and walls of the first electrode chamber;
   a second electrode chamber, and a second solid state electrode located inside the second electrode chamber such that a second cavity is formed between the second solid state electrode and walls of the second electrode chamber, the first and the second solid state electrodes are configured to generate the electric field for the impedance measurement of the flowing particles;
   a first conduit providing a fluid communication between the first cavity of the first electrode chamber and the channel so that the liquid from the channel can contact the first solid state electrode via the first conduit and the first cavity;
   a second conduit providing a fluid communication between the second cavity of the second electrode chamber and the channel so that the liquid from the channel can contact the second solid state electrode via the second conduit and the second cavity; and
   an electric connection from at least one of the first and the second solid state electrodes, the electric connection connected to a measurement instrument for the impedance measurement,
   wherein at least one of the first and the second solid state electrode has a tapered shape that becomes narrower towards the channel, an end of the tapered shape facing the channel forming a surface that is parallel to the channel, and the parallel surface is not located inside the channel.

2. The impedance measurement device of claim 1, wherein at least one of a portion of the first electrode chamber becomes narrower with a decreased distance towards the channel, and a portion of the second electrode chamber becomes narrower with a decreased distance towards the channel.

3. The impedance measurement device of claim 1, wherein no portion of the first and second solid state electrodes are located in the channel but a portion of the first and second solid state electrodes are located in the first and second conduits, respectively.

4. The impedance measurement device of claim 3, wherein the first and second conduits are both arranged perpendicular to a longitudinal extension of the channel.

5. The impedance measurement device of claim 2, wherein the first and second solid state electrodes are configured to be operated for current injection.

6. The impedance measurement device of claim 2, wherein the first and second solid state electrodes are configured to be operated for voltage measurement.

7. The impedance measurement device of claim 1, wherein at least one of the first conduit and second conduit includes vertical obstacles to minimize flow at the first and the second conduit.

8. The impedance measurement device of claim 1, further comprising:
   a third electrode chamber, and a third solid state electrode located inside the third electrode chamber such that a third cavity is formed between the third solid state electrode and walls of the third electrode chamber;
   a fourth electrode chamber, and a fourth solid state electrode located inside the fourth electrode chamber such that a fourth cavity is formed between the fourth solid state electrode and walls of the fourth electrode chamber;
   a third conduit providing a fluid communication between the third cavity of the third electrode chamber and the channel;
   a fourth conduit providing a fluid communication between the fourth cavity of the fourth electrode chamber and the channel; and
   a working zone cavity located downstream of the first and second conduits, and upstream of the third and fourth conduits.

9. The impedance measurement device of claim 8, wherein the working zone cavity has a meandering shape.

10. The impedance measurement device of claim 1, further comprising:
    a branching channel in fluid communication with the channel,
    wherein the first and second electrode chambers and the first and second conduits are located on one side of the channel, and the branching channel is located on another side of the channel, in an area between the first and second conduits.

11. The impedance measurement device of claim 1, wherein the first and second electrode chambers have walls that are made of gas-permeable material.

12. The impedance measurement device of claim 1, wherein the flowing particles are cells.

13. The impedance measurement device of claim 1, wherein the first and second solid state electrodes are patterned onto the walls of the first and second electrode chambers, respectively.

14. The impedance measurement device of claim 1, wherein the first conduit provides a separation between the first solid state electrode and the channel, and the second conduit provides a separation between the second solid state electrode and the channel.

15. The impedance measurement device of claim 1, wherein at least one of the first and the second solid state electrode has a tapered shape that becomes narrower towards the channel, an end of the tapered shape facing the channel forming a rectangular-shaped electrode portion.

16. The impedance measurement device of claim 15, wherein no portion of the rectangular-shaped electrode portion is located inside the channel.

17. The impedance measurement device of claim 1, wherein a portion of the at least one of the first and the second solid state electrodes has a triangular shape, a side wall of the triangular shape is exposed to the at least one first and second cavity, respectively.

18. The impedance measurement device of claim 1, wherein no electrodes are arranged inside the channel for impedance measurement.

19. An impedance measurement device for measuring an impedance of flowing particles by an electric field, comprising:
- a channel for conducting a liquid with the flowing particles;
- a first electrode chamber, and a first solid state electrode located inside the first electrode chamber such that a first cavity is formed between the first solid state electrode and walls of the first electrode chamber;
- a second electrode chamber, and a second solid state electrode located inside the second electrode chamber such that a second cavity is formed between the second solid state electrode and walls of the second electrode chamber, the first and the second solid state electrodes are configured to generate the electric field for the impedance measurement of the flowing particles;
- a first conduit providing a fluid communication between the first cavity of the first electrode chamber and the channel so that the liquid from the channel can contact the first solid state electrode via the first conduit and the first cavity;
- a second conduit providing a fluid communication between the second cavity of the second electrode chamber and the channel so that the liquid from the channel can contact the second solid state electrode via the second conduit and the second cavity; and an electric connection from at least one of the first and the second solid state electrodes, the electric connection connected to a measurement instrument for the impedance measurement,
- wherein at least one of the first and the second solid state electrode has a tapered shape that becomes narrower towards the channel, and an end of the tapered shape facing the channel forms a rectangular-shaped electrode portion.

20. An impedance measurement device for measuring an impedance of flowing particles by an electric field, comprising:
- a channel for conducting a liquid with the flowing particles;
- a first electrode chamber, and a first solid state electrode located inside the first electrode chamber such that a first cavity is formed between the first solid state electrode and walls of the first electrode chamber;
- a second electrode chamber, and a second solid state electrode located inside the second electrode chamber such that a second cavity is formed between the second solid state electrode and walls of the second electrode chamber, the first and the second solid state electrodes are configured to generate the electric field for the impedance measurement of the flowing particles;
- a first conduit providing a fluid communication between the first cavity of the first electrode chamber and the channel so that the liquid from the channel can contact the first solid state electrode via the first conduit and the first cavity;
- a second conduit providing a fluid communication between the second cavity of the second electrode chamber and the channel so that the liquid from the channel can contact the second solid state electrode via the second conduit and the second cavity; and
- an electric connection from at least one of the first and the second solid state electrodes, the electric connection connected to a measurement instrument for the impedance measurement,
- wherein a portion of the at least one of the first and the second solid state electrodes has a triangular shape, and a side wall of the triangular shape is exposed to the at least one first and second cavity, respectively.

* * * * *